(12) United States Patent
Reddy et al.

(10) Patent No.: US 11,674,942 B1
(45) Date of Patent: Jun. 13, 2023

(54) SENSOR ASSEMBLY

(71) Applicant: Swim Sense, LLC, Pompano Beach, FL (US)

(72) Inventors: Rakesh Reddy, Boca Raton, FL (US); Kevin Doyle, Pompano Beach, FL (US)

(73) Assignee: Swim Sense, LLC, Pompano Beach, FL (US)

( * ) Notice: Subject to any disclaimer, the term of this patent is extended or adjusted under 35 U.S.C. 154(b) by 0 days.

(21) Appl. No.: 17/963,752

(22) Filed: Oct. 11, 2022

(51) Int. Cl.
*G01N 33/18* (2006.01)

(52) U.S. Cl.
CPC .................................. *G01N 33/18* (2013.01)

(58) Field of Classification Search
CPC ........................................................ G01N 33/18
USPC .................................... 73/64.56, 61.59, 431
See application file for complete search history.

(56) References Cited

U.S. PATENT DOCUMENTS

| | | | |
|---|---|---|---|
| 7,695,613 B2 | 4/2010 | Doyle | |
| 9,416,034 B2 | 8/2016 | Johnson | |
| 9,834,451 B2 | 12/2017 | Miller | |
| 10,472,263 B2 | 11/2019 | Johnson | |
| 10,492,268 B2 | 11/2019 | Potucek | |
| 10,737,951 B2 | 8/2020 | Miller | |
| 10,801,225 B1 | 10/2020 | Reddy | |
| 11,097,958 B2 | 8/2021 | Miller | |
| 11,108,585 B2 | 8/2021 | Khalid | |
| 2014/0273052 A1* | 9/2014 | Reddy | G01N 33/1893 436/164 |
| 2016/0123950 A1* | 5/2016 | Howes, Jr. | G01N 27/4168 73/61.59 |
| 2016/0340205 A1 | 11/2016 | Murdock | |
| 2018/0240322 A1 | 8/2018 | Potucek | |
| 2018/0273404 A1 | 9/2018 | Denkewicz, Jr. | |
| 2019/0105226 A1 | 4/2019 | Potucek | |
| 2019/0158307 A1 | 5/2019 | Khalid | |
| 2020/0270889 A1 | 8/2020 | Buosanto | |
| 2021/0380435 A1 | 12/2021 | Miller | |

FOREIGN PATENT DOCUMENTS

| | | |
|---|---|---|
| AU | 2022200316 | 2/2022 |
| WO | WO2021091773 | 5/2021 |

* cited by examiner

*Primary Examiner* — Nathaniel J Kolb
(74) *Attorney, Agent, or Firm* — Clayton, McKay & Bailey, PC

(57) ABSTRACT

A sensor assembly may include a chassis, cover, first sensor, second sensor, and a control system. The chassis may include a first housing that defines a chamber with the cover and includes a partition within the chamber. A second housing of the chassis may define first and second ports in fluid communication with the chamber. A central wall may extend from an inner surface of the second housing and a protruding wall may extend over the central wall. Both the partition and the central wall may extend from locations along a longitudinal axis of the sensor assembly that are between the first port and the second port. In some examples the protruding wall and the partition direct a portion of fluid flowing within the second housing into and out of the chamber, and the first and second sensors detect values for respective fluid parameters for the portion of fluid.

20 Claims, 13 Drawing Sheets

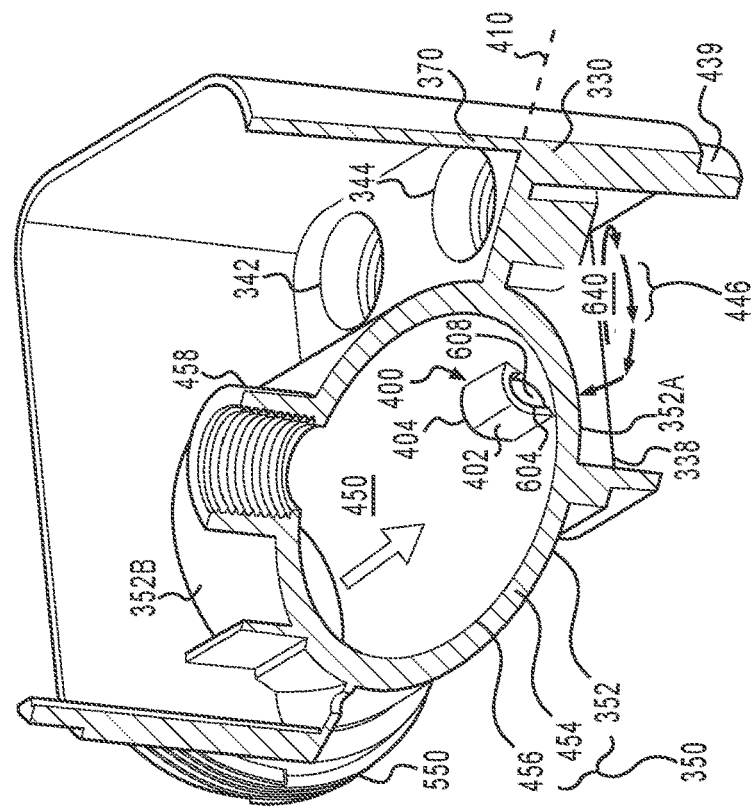
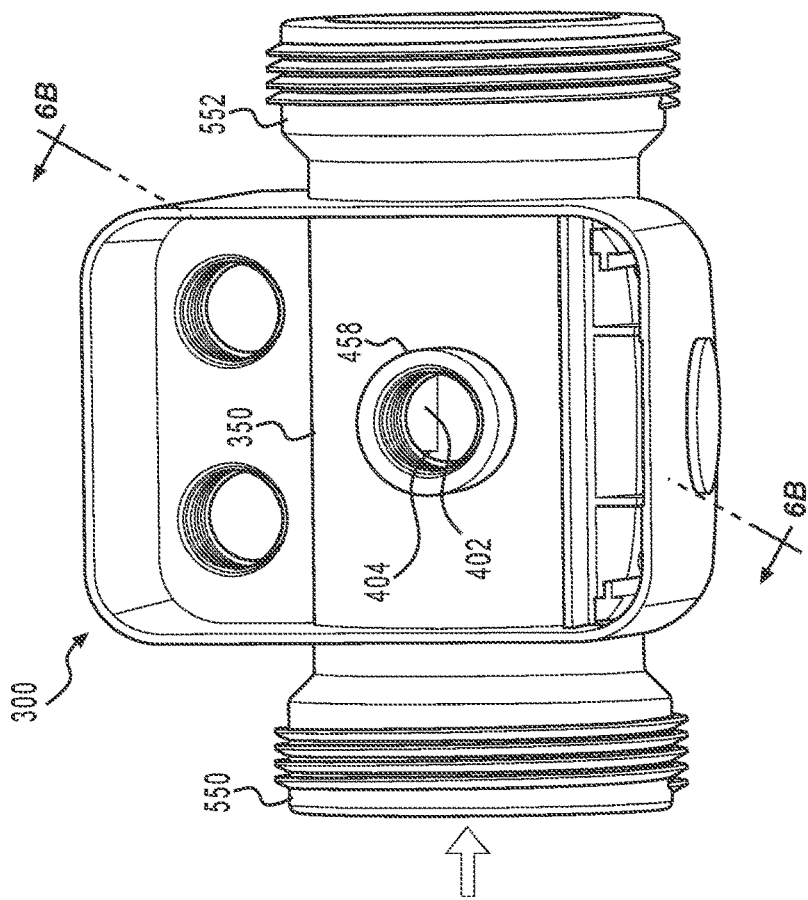
FIG. 6B
FIG. 6A

SENSOR ASSEMBLY

BACKGROUND

In many fluid systems, such as many pool/spa systems, levels of various chemicals are tracked and regulated. In some fluid systems including a chemical sensing system, fluid may be pumped through a filter, a chlorinator, and an acid dispenser. Other devices such as valves and heat pumps may also be included. Some chemical sensing systems may include some type of container plumbed on two sides of the filter. In some examples, this may be accomplished with: (1) a first tube fluidly connected to the container and cut in and attached to a fluid carrying conduit upstream of the filter; and (2) a second tube fluidly connected to the container and cut in and attached to the fluid carrying conduit downstream of the filter. In turn, a differential pressure may be created that causes the fluid to circulate through the container where it may be subject to analysis by various sensors.

Such chemical sensing systems as previously described may require: specific construction materials; specific devices and operational materials (e.g., specific types of probes and chemicals for probe operation); an appreciable or significant amount of space, skilled installers or a number of additional installers; and/or significant time that is in addition to what would be required to install a fluid system without such a chemical sensing system. In addition, such systems may require special procedures for continued operation and maintenance. As a result of the complexities, space requirements, and/or costs associated with installation, operation, and maintenance of these chemical sensing systems, such systems are typically only implemented in commercial settings. This is especially the case for fluid systems for pools, spas, or pool and spa combinations.

As a result, a need exists for devices, systems, and methods dedicated to determining concentrations of various chemicals in commercial and non-commercial fluid systems that are not complicated, large, or require expertise for installation and maintenance. In particular, a need exists for chemical concentration determining devices, systems, and methods that can be installed and used in non-commercial fluid systems, such as those implemented in pools and spas for residential applications, without significant cost, time, expertise, or additional components or devices.

SUMMARY

Examples described herein include device components, devices, systems, and methods for measuring multiple fluid parameters for a fluid being conveyed through a fluid system.

In one example, a chassis for a sensor assembly may include a first housing including a first wall, a second wall, and side walls that define a chamber that is open at one end. A second housing may include an inner surface, an outer surface, and a body extending between the inner surface and the outer surface. In one example, the inner surface may define a conduit that extends along a longitudinal axis of the second housing. The conduit may provide a pathway for a majority of a fluid flowing through the sensor assembly to pass. In another example, the body may define first and second ports that that extend through the body, and the outer surface may be attached to the first housing. A central wall may extend from the inner surface between the first port and the second port along the longitudinal axis. In addition, a protruding wall may extend inwardly from the inner surface into the conduit and over the central wall. In one example a partition may extending between the first wall and the second wall of the first housing in a location along the longitudinal axis that is between the first port and the second port. In other examples, for fluid flowing through the chamber, the first housing may be configured to receive a first sensor that measures a first fluid parameter and a second sensor that measures a second fluid parameter.

In some examples a sensor assembly may include a chassis, a cover, a first sensor for a first fluid parameter, a second sensor for a second fluid parameter, and a control system. In some examples, the cover may be attached to the chassis and include an inner surface that defines a chamber along with a housing of the chassis. In other examples, the first and second sensors may extend into the chamber.

In some examples, a chassis may include a first housing and a second housing. The first housing may include a first wall, a second wall, and side walls that define a chamber along with an inner surface of a cover. Further, the first housing may be attached to the second housing. The second housing may extend along a longitudinal axis and include a body that extends between an inner surface and an outer surface. The body may define first and second ports that extend therethrough and establish fluid communication between the chamber and a conduit defined by the inner surface of the second housing.

In other examples, a chassis may include a first housing that defines a chamber and a second housing attached to the first housing. The second housing may include a central wall, a protruding wall, and a partition. The central wall may extend from an inner surface at a location along the longitudinal axis of a sensor assembly that is between a first and second ports that are defined by the body and in fluid communication with the chamber. The protruding wall may extend inwardly from the inner surface over the central wall, and a partition may extend between a first wall and a second wall of the first housing at a location along the longitudinal axis that is between the first port and the second port.

In some examples, a sensor assembly may include a control system that is configured to communicate with first and second sensors disposed in a chamber defined by a first housing and a cover of the sensor assembly. The control system may transmit information associated with first and second fluid parameters respectively measured by the first and second sensors, based on communications with the first and second sensors. In one example, a protruding wall and a partition of a second housing attached to the first housing, may direct a portion of fluid flowing through the sensor assembly into the chamber, by the first and second sensors, and out of the chamber. The first and second sensors may detect values for the first and second fluid parameters for the portion of fluid.

In still other examples, a method of measuring parameters of fluid flow may include installing a sensor assembly in a fluid system in an inline arrangement and operating the first and second sensors as a fluid flows through the sensor assembly as part of the fluid system. In other examples, the method may include transmitting information associated with the first and second fluid parameters with a control system of the sensor assembly. Transmitting by the control system may be based on operations of the first and second sensors and communications between the control system and the first and second sensors. In one example of the method, the sensor assembly may include a chassis, a cover, and the first and second sensors attached to the chassis. The chassis may include first and second housings. The first housing may define a chamber along with the cover, and include a partition disposed with the chamber. The second housing may include an inner surface that defines a conduit, an outer surface attached to the first housing, and a body that defines first and second ports. In some examples, a central wall may extend from the first inner surface between the first and second ports, and a protruding wall may extend from the inner surface over the central wall. In some examples operating the first and second sensors may include directing a portion of the fluid to the first and second sensors as the fluid flows through the second housing, and the directing may include directing the portion with the protruding wall and the partition into the chamber, past the first and second sensors, and out of the chamber.

The examples summarized above can each be incorporated into a non-transitory, computer-readable medium having instructions that, when executed by a processor associated with a computing device, cause the processor to perform the stages described. Additionally, the example methods summarized above can each be implemented in a system including, for example, a memory storage and a computing device having a processor that executes instructions to carry out the stages described.

Both the foregoing general description and the following detailed description are exemplary and explanatory only and are not restrictive of the examples, as claimed.

BRIEF DESCRIPTION OF THE DRAWINGS

FIG. 6A illustrates an overhead view of a chassis of a sensor assembly according to an aspect of the present disclosure.

FIG. 6B is a sectional view of the chassis of FIG. 6A taken from a plane indicated by line 6B-6B.

DESCRIPTION OF THE EXAMPLES

Reference will now be made in detail to the present examples, including examples illustrated in the accompanying drawings. Wherever possible, the same reference numbers will be used throughout the drawings to refer to the same or like parts.

Figure 1:
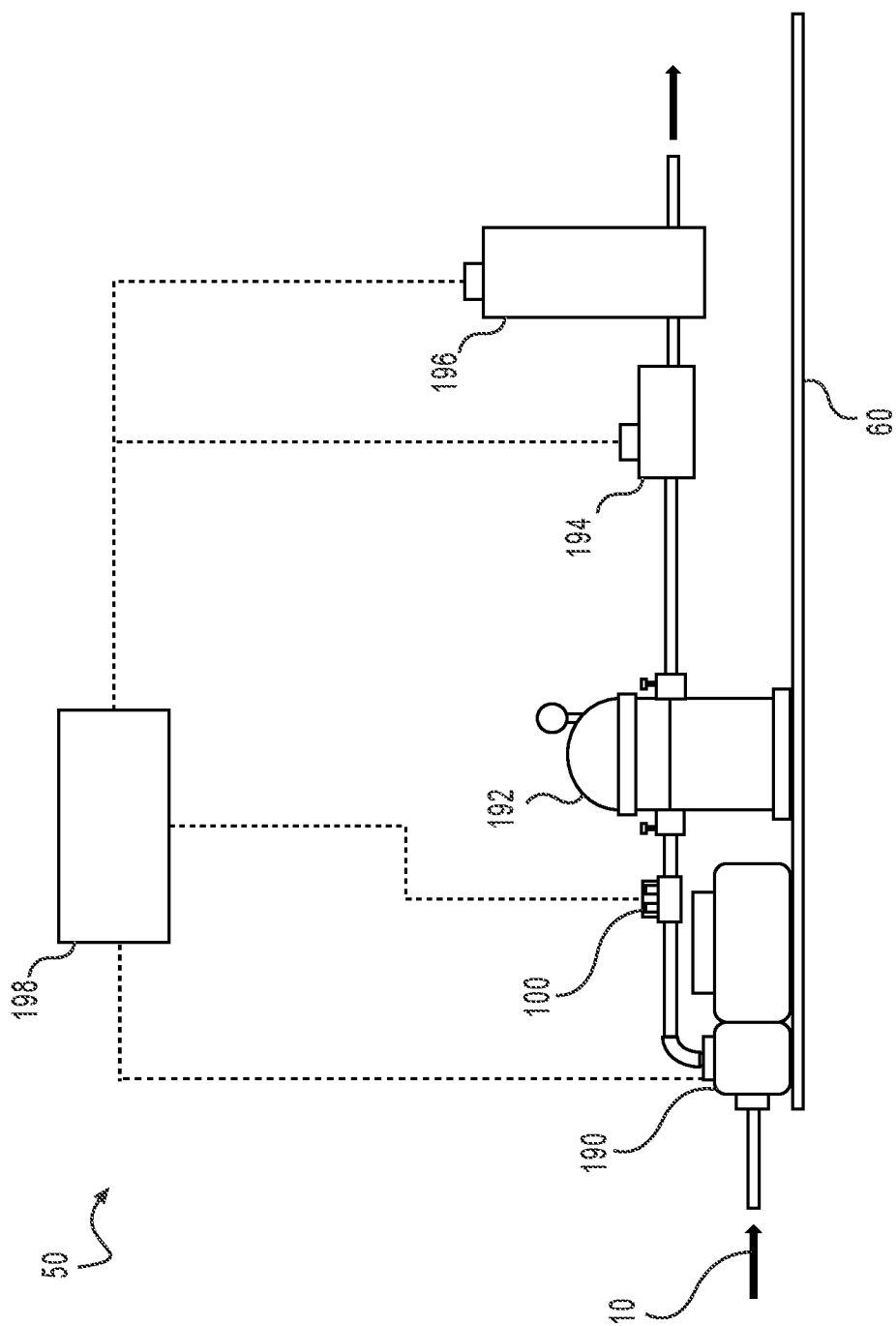
FIG. 1 is an illustration of exemplary system components for measuring multiple parameters of a fluid flowing through a fluid system with a sensor assembly, according to an aspect of the present disclosure.

FIG. 1 is an illustration of exemplary system components for measuring multiple parameters of a fluid flowing through a fluid system 50 with a sensor assembly 100, according to an aspect of the present disclosure. In one example, the fluid system 50 may define a portion of a fluid circuit that circulates fluid as part of an overall operation of a particular feature, an apparatus, or fluid application, such as a pool and/or a spa (not shown). The fluid system 50 may include a pump 190 and a filter 192 mounted to a pad 60, a chlorinator 194 fluidly connected to an outlet end of the filter 192, and an acid dispenser 196 downstream of the chlorinator 166. Fluid may flow in a flow direction 10 into the pump 190 from a pool, a spa, or other fluid system component and be output under pressure by the pump 190 to the sensor assembly 100 prior to flowing through the filter 192, chlorinator 194, and acid dispenser 196.

The fluid system 50 further includes a panel 198, such as a fluid system panel ("panel") or some type of management controller known in the art, that is configured for installation in fluid systems, to initiate, monitor, and control functions of equipment generally responsible for, or encompassing of, overall fluid system operation. The panel 198 may be communicatively connected (directly) to the pump 190, the sensor assembly 100, the chlorinator 194, and the acid dispenser 196 via connectors, wires, optical devices, additional panels, device-specific controllers, management controllers, or the like, suitable for carrying data, and in some cases transmitting power, between devices. It will be understood that connections between the panel 198 and any or all other system components may include any type of data carrying device and may be different from one another. In addition, each connection may be specific to the fluid system components communicatively connected thereby.

Turning to the operation of the fluid system 50, fluid may flow under pressure to an inlet of the pump 190. The pump 190, under the control of the panel 198, conveys the fluid to the sensor assembly 100. A portion of the fluid may be directed through an inlet of a diverter into a chamber of the sensor assembly 100 that includes one or more sensors. Such chambers, sensors, and diverters are discussed in more detail with reference to the various example sensor assembly is described hereafter. The portion of the fluid directed into the chamber will flow past the sensors, out of a diverter outlet, and into the primary flow of the fluid as it passes through the sensor assembly 100. The fluid may then be conveyed in the flow direction 10 into the filter 192 and through the chlorinator 194 and acid dispenser 196. From the acid dispenser 196, the fluid may be circulated through a remainder of the fluid system 10 not shown, such that at least a portion of the fluid is returned to and subsequently conveyed by the pump 190.

In one example, control of the pump 190, the chlorinator 194, and/or the acid dispenser 196 by the panel 198 may be dependent upon or otherwise responsive to information from the sensor assembly 100, as received, processed, and interpreted by the control component 198. In particular, control of one or more fluid system components, including the pump 190, chlorinator 194, and the acid dispenser 196, may be directly responsive to (i.e., able to be processed without any intermediary processing by a component other than the sensor assembly) information output by the sensor assembly 100. Furthermore, this output may be transmitted directly to a particular fluid system component from the sensor assembly 100 or through the control component 198.

In one example, sensors provided in the chamber of the sensor assembly 100 may include a probe for measuring the power of Hydrogen ("pH") and a probe for measuring Oxidation Reduction Potential ("ORP"). In other examples, the sensor assembly 100 may include some combination of sensors that detect salinity, alkalinity, dissolved oxygen, water hardness, nitrates, calcium, etc. In addition to the probes discussed above, the sensor assembly may include temperature and flow sensors in the chamber and/or main pathway through the sensor assembly 100. For example, in an exemplary version of the sensor assembly 100 that includes pH and ORP sensors, the control component 198 may manage the operation of the chlorinator 194 and acid dispenser 196 based on fluid pH and ORP readings from the sensor assembly 100.

As noted above, in one example of the fluid system 10, the chlorinator 194 and acid dispenser 196 may be controlled based on the information from the sensor assembly 100. This type of fluid system configuration thus provides "sense and dispense" capabilities. Sensor assemblies of the present disclosure provide particular advantages in the context of sense and dispense systems. More specifically, each of the sensor assemblies described herein include structural configurations that provide an "on-the-pipe" (see FIGS. 2-3B, 9-10B, and 12-14) installation capability, and a self-contained sensing chamber (see FIGS. 3A, 3B, 4, 10A, 10B, and 13).

As will be apparent from the description below, these features may eliminate a need to provide one or more stand-alone chambers, each including one or more sensors, that are connected to conduits that are separately plumbed into a main line—as in a bypass type of configuration. Such a complex combination of components could potentially be cost-prohibitive or not possible due to space constraints in, for example, a pool and spa fluid system installed in a non-commercial (e.g., residential) setting where a sense and dispense system could be used (e.g., for deploying chlorine and acid).

The "on-the-pipe" feature essentially translates to any of the sensor assemblies described herein, may in essence, replace a portion of a main pipe, conduit, or other direct fluid connection between, for example, a pump and another fluid system component, such as a filter. Thus, all the sensor assemblies described herein may be installed between and in-line with fluid system components, absent any type of additional "off-the-pipe" conduit/piping (e.g., as in a bypass line piped into but completely/spatially separate from a main line). Further, any of the exemplary sensor assemblies according to the present disclosure may include a diverter that serves to capture a portion a main flow of fluid, direct that portion through a chamber (self-contained sensor chamber) including one or more sensors, and further direct that fluid portion back into the main flow of fluid. Thus, the sensor assemblies according to the present disclosure provide both a portion of a fluid connection between fluid system components, and a bypass and return path for a portion of fluid from which certain parameters may be measured by the sensors installed in the chamber of the sensor assembly.

Figure 2:
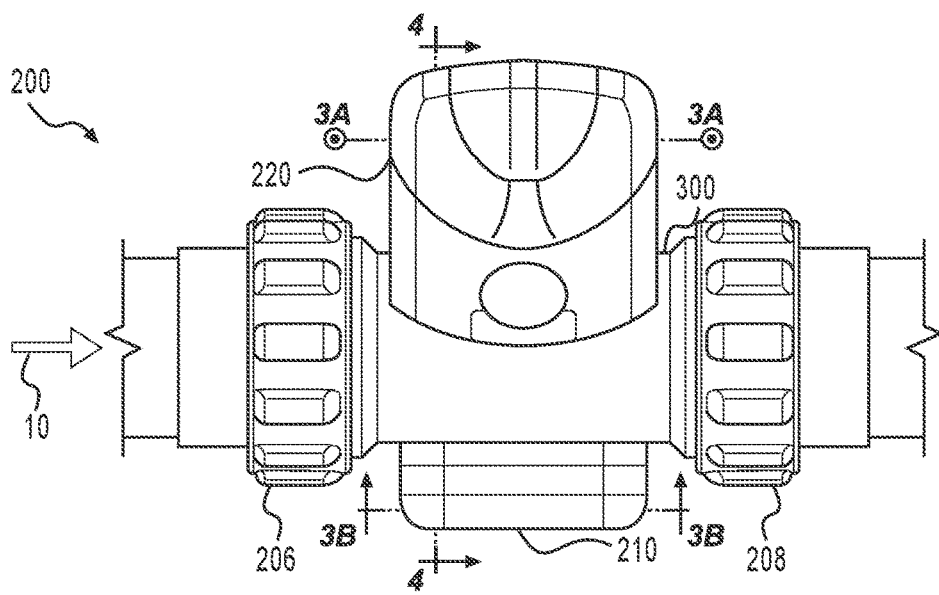
FIG. 2 illustrates a front perspective view of an exemplary sensor assembly according to an aspect of the present disclosure.
Figure 3A:
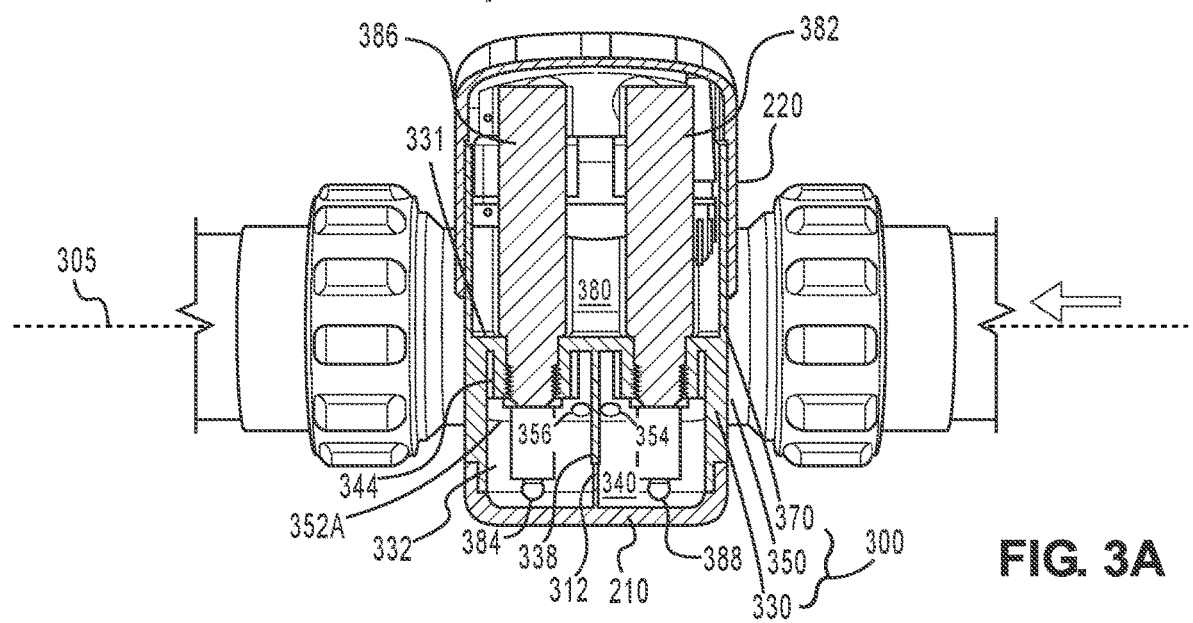
FIG. 3A is a sectional view of the sensor assembly of FIG. 2 taken from a distal plane "looking out of the page" as indicated by line 3A-3A.
Figure 3B:
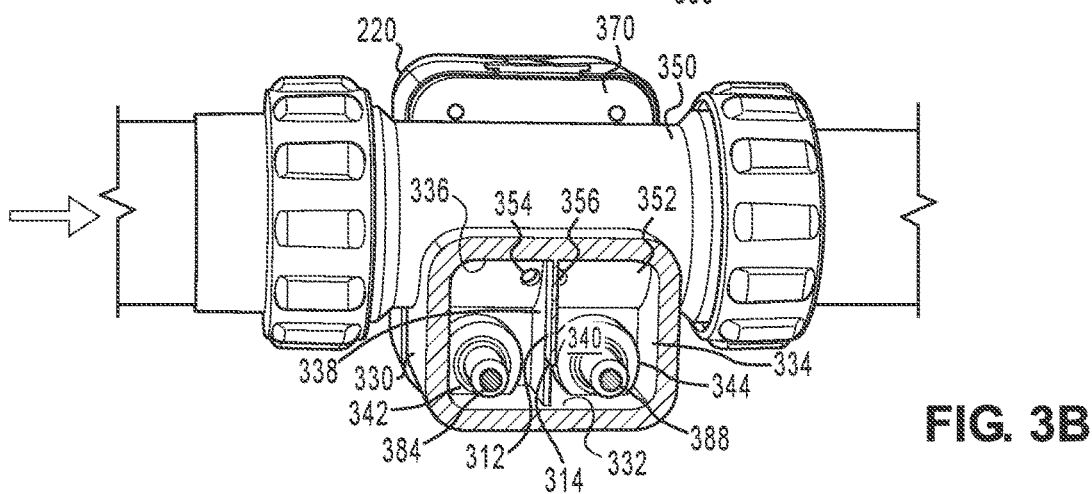
FIG. 3B is a sectional view of the sensor assembly of FIG. 2 taken from a plane indicated by line 3B-3B.

FIG. 2 illustrates a front perspective view of an exemplary sensor assembly 200 according to an aspect of the present disclosure. FIGS. 3A and 3B are sectional views of the sensor assembly 200 of FIG. 2 taken from planes indicated by lines 3A-3A and 3B-3B respectively. As shown in FIG. 2, the sensor assembly 200 includes a chassis 300, a first cover 210, and a second cover 220. As used herein, the term "chassis" may be used to describe a supporting body, frame, or other type of structure for an assembly of components, or a core structure of a single body. In one example, the chassis 300 may be secured to opposing conduits by first and second adapters 206, 208 respectively attached to opposite ends of the sensor assembly 200.

For the purposes of the present disclosure a flow direction indicator 10, and other such direction indicators included in the figures of the present disclosure without a numeral designation, may correspond to a preferred direction of fluid flow through a respective exemplary sensor assembly of the present disclosure. A direction of any flow direction indicator may correspond to a standard and continuous operating condition of a sensor assembly associated with that flow direction indicator (as illustrated), as that exemplary sensor assembly may be installed and operated within a respective fluid system. However, it will be understood that the sensor assembly 200 may operate to provide measurements of the various fluid parameters discussed herein should fluid flow through any of the sensor assemblies in a direction opposite to that of a respective flow direction indicator. Thus, the sensor assemblies of the present disclosure may function as intended when a direction of fluid flow through a fluid system is reversed, for example during a backwash operation for a pool or spa.

FIG. 3A is a sectional view that is taken from a distal plane indicated by line 3A-3A looking out of the page. As illustrated in FIG. 3A, the chassis 300 includes first, second, and third housings 330, 350, 370. Along with the first cover 210, the first housing 330 defines a first chamber 340 in which sensor probes 384, 388 may be positioned and exposed to a portion of an overall flow of fluid flowing through the sensor assembly 200. On the other hand, the second housing 350 may define a fluid conduit through which the majority of fluid passing through the sensor assembly 200 flows (as well as the portion of the fluid in the first chamber 340 before and after that portion flows through the first chamber 340). The third housing 370 and the second cover 220 may define a second chamber 380 in which other sensors and assembly components (e.g., antenna, printed circuit board, BLUETOOTH components, WiFi components, etc.) may be disposed.

The first housing 330 further defines a first partition 338 that corresponds to a second partition 212 extending from an inner surface 418 (see FIG. 4) of the first cover 210. In one example, the second partition 212 may be sized to tightly abut against an edge of the first partition 338. In another example, the edge may define a slot that corresponds in thickness to a thickness of the second partition 212 which fits into the slot when the first cover 210 is attached to the first housing 330 of the chassis 300.

As shown in FIGS. 3A and 3B, the first partition 338 extends from a first wall 332 of the first housing 330, across an entirety of the first chamber 340, to a second wall 336 of the first housing 330. On the other hand, the second partition 212 extends from a wall of the first cover 210 corresponding to the first wall 332 of the first housing 330, across only a portion of the first chamber 340, and thereby defines a chamber port 448 (see FIG. 4). As discussed below, the chamber port 448 ensures fluid communication is maintained between the chamber inlet 354 and a chamber outlet 356 defined by the second housing 350. Along a longitudinal axis 305 of the sensor assembly 200 (as well as the second housing 350), the first and second partitions 338, 312 may be disposed between the chamber inlet 354 and the chamber outlet 356. This also means that the first and second partitions 338, 312 are disposed along the longitudinal axis 305 between first port 408/diverter inlet 404 and the second port 608/diverter outlet 604 (see FIGS. 4 and 6).

In one example, the first housing 330 may define first and second apertures 342, 344 disposed on opposite sides of the first partition 338. As shown, surfaces of the first housing 330 that defines the first and second apertures 342, 344 may be formed, structured, or otherwise provided to include some type of interlocking structure (e.g., threads, slots, snap-fit components, etc.). In particular, each of the first and second apertures 342, 344 define a threaded surface as shown, which is configured to receive and secure a corresponding threaded surface of a sensor, such as the first or second sensor 382, 386. It will be understood that an interlocking/fastening structure of the first aperture 342 may differ from an interlocking/fastening structure of the second aperture 344.

Figure 4:
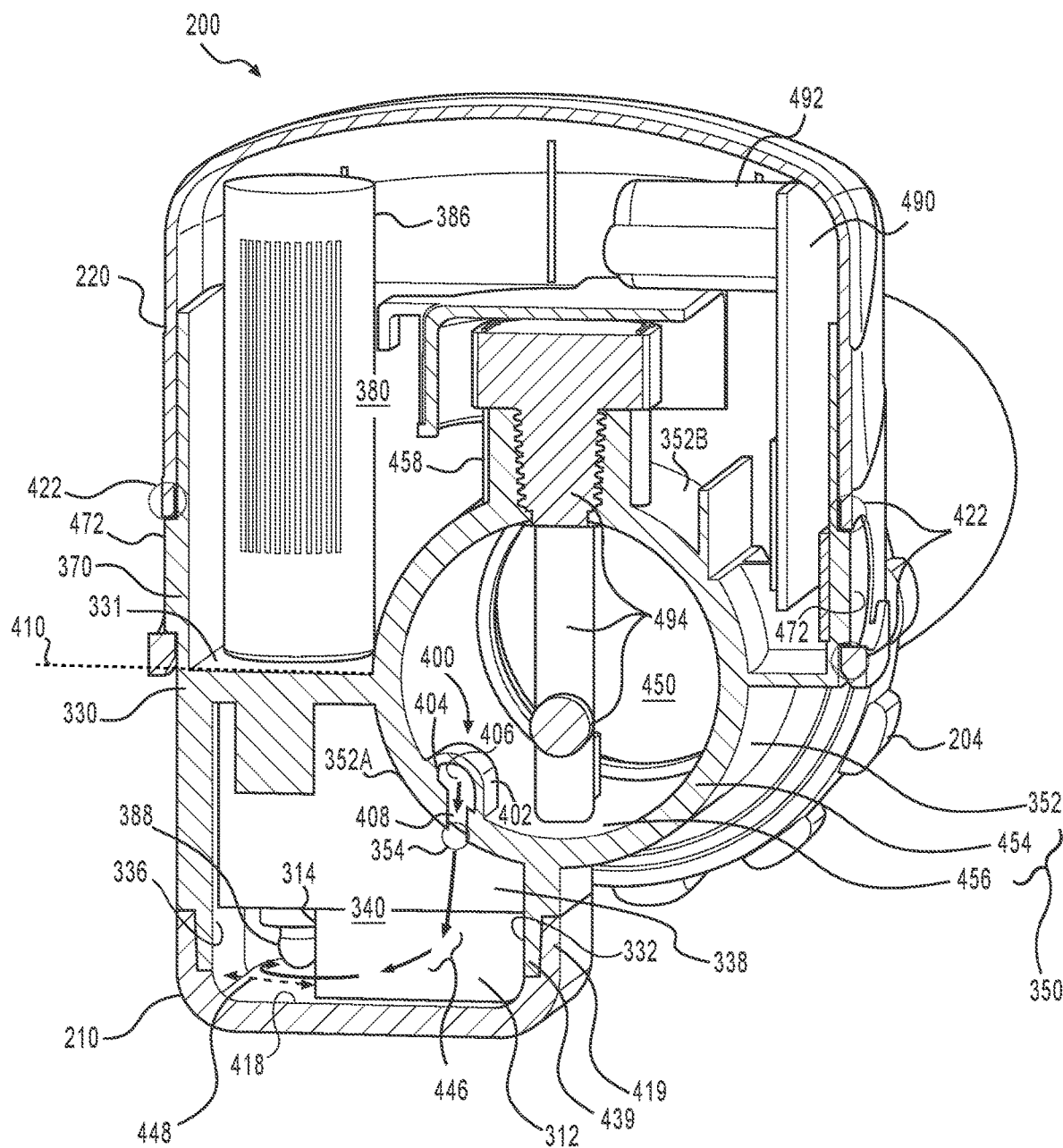
FIG. 4 is a sectional view of the sensor assembly of FIG. 2 taken from a plane indicated by line 4-4.

FIG. 4 is a sectional view of the sensor assembly 200 of FIG. 2 taken from a plane indicated by line 4-4 and shows cross-sections of the first and second covers 210, 220 and the chassis 300, including cross-sections of the first housing 330 and a body 454 of the second housing 350. FIG. 4 further illustrates a line of demarcation 410 between the first housing 330 and the third housing 370 at the upper end-face 331 of the first housing 330.

The first cover 210 may be secured to the first housing 330 of the chassis 300 via an interlocking, press, or snap fit provided between a stepped wall 419 of the first cover 210 and a lip 439 defined on a bottom end-face of the first housing 330. In one example, the fit between the first cover 210 and the first housing 330 may enable attachment, removal, and reattachment of the first cover 210 to the first housing 330.

Regarding the second cover 220, raised surfaces 472 are provided on opposite sides of the third housing 370 and configured to engage the tabs 422 of the second cover 220 when the second cover 220 is slid onto the chassis 300. In doing so, the tabs 422 effectively secure the second cover 220 to the chassis 300 but also provide a simple mechanism for removal. In particular, the tabs 422 may be pushed or pulled by hand to disengage the raised surfaces 472 and thereby free the second cover 220 to be lifted relative to and removed from the chassis 300.

As shown in FIG. 4, the body 454 of the second housing 350 extends from an inner surface 456 to an outer surface 452, is cylindrical, and defines a conduit 450 through which fluid may flow. The outer surface 452 of the second housing 350 is divided by the first housing 330 into first and second segments 352A, 352B. The first segment 352AA defines a wall of the first chamber 340 including the chamber inlet 354 and the chamber outlet 356 (see FIGS. 3A and 3B). The second segment 352B defines a wall of a portion of the second chamber 380 in which the sensors 382, 386 are disposed. The second segment 352B also may define one wall of another portion of the second chamber 380 in which a printed circuit board ("PCB") of a sensor assembly control system, may be disposed. An exemplary sensor assembly control system ("SACS") is discussed in more detail with reference to FIG. 11.

The inner surface 456 of the second housing 350 defines a diverter 400 that protrudes into a conduit 450 defined by the inner surface 456 of the second housing 350. As shown in FIG. 4, the diverter 400 includes a protruding wall 402 that defines a diverter inlet 404 along with a central wall 406. The central wall 406 separates the diverter inlet 404, which is in fluid communication with the chamber inlet 354 via a first port 408 of the diverter 400, from a diverter outlet 604 illustrated in FIG. 6B. The first port 408 is defined within the body 454 of the second housing 350. The diverter outlet 604 is in fluid communication with the chamber outlet 356 via a second port 608 of the diverter 400, which is also defined within the body 454 of the second housing 350 (see FIGS. 6A and 6B).

The diverter 400 provides a mechanism within a fluid flow path defined by the second housing that directs or otherwise causes fluid to enter the first chamber 340 through the first port 408 and exit the first chamber 340 through the second port 608. The diverter inlet 404 which is in direct fluid communication with the first port 408, faces against a fluid flow direction. The diverter outlet 604, which is in direct fluid communication with the second port 608, faces the same direction as a fluid flow direction. This ensures a flow rate of the fluid flow generates adequate flow into, through, and out of the first chamber 340. In on example, the diverter 400 may have a filter disposed at the diverter inlet 404 or within the first port 408 to prevent any debris from entering the first chamber 340.

One of ordinary skill in the art will recognize that a size of the diverter inlet 404 and/or the first port 408, may be smaller or larger than the second port 608 and/or the diverter outlet 604 to provide an optimal fluid flow through the first chamber 340. In one example, optimal fluid flow may correspond to a fluid flow rate that ensures the most consistent and accurate readings are generated by probes of sensors, and may depend on the type sensors (e.g., pH, ORP, Alkalinity, dissolved oxygen, etc.) incorporated in the sensor assembly 200.

A fluid passage 446 is defined by the diverter inlet 404, the first port 408, the chamber inlet 354, first and second partitions 338, 312, first and second walls 332, 334 of the first housing 330, the inner surface 418 the first cover 210, and as shown in FIG. 6B, the chamber outlet 356, second port 608, and diverter outlet 604. An inflow portion of the fluid passage 446 is shown in FIG. 4, and an outflow portion (except for those portions defined by the first cover 210) of the fluid passage 446 is shown in FIG. 6B.

The first and second partitions 338, 312 are disposed within the first chamber 340 downstream of the diverter and chamber inlets 404, 354, and upstream of the chamber and diverter outlets 356, 604. With this arrangement of inlets, partitions, and outlets, fluid entering the diverter inlet 404 may be accompanied by the creation of a pressure differential (high to low) across the first chamber 340 from the inflow portion to the outflow portion of the fluid passage 446. In turn, a fluid flowing into the diverter inlet 404 may flow through the first chamber 340, past the first and second probes 384, 386 and through the diverter outlet 604 to rejoin with a main flow of fluid flowing through the second housing.

Thus, in practice, the diverter 400 may direct fluid into the first chamber 340, a reservoir-like enclosed space; cause the fluid to contact with first and second probes 384, 388; enable flow of that same fluid past the probes and out of the first chamber 340 and into the second port 608; and finally exit the diverter 400 through the diverter outlet 604. The diverter 400 accomplishes this without requiring separate conduits plumbed to a fluid system on upstream and downstream sides of a fluid system component, such as a filter, so that a differential pressure to cause fluid to circulate through a device that is completely separated from a fluid circuit of the fluid system that includes the fluid system component. Unlike fluid systems incorporating a sensor assembly according to the present disclosure, such a system requires complex connections between conduits that must be plumbed to carry fluid into the chamber. Such complexities present barriers for widespread application to certain fluid systems that are ubiquitous, such as residential pool and spa fluid systems.

Accuracy of certain types of sensors that detect various parameters associated with a fluid (e.g., salinity, pH, ORP, alkalinity, etc) and a flow of the fluid (e.g., flow rate, volume, pressure, etc.) may be affected by turbulent flow. For example, a high degree of turbulence can cause a pH or an ORP sensor to produce inconsistent values. Further, the turbulent flow can also cause faster drift in these examples because of faster leaching of the reference electrode solution used by the pH and ORP electrodes. In addition, air bubbles can occur in a flow of fluid as a matter of course or as a by-product of turbulent flow. In either scenario, air bubbles can cause sensors, such as those that may be installed in the sensor assembly 200, to produce erroneous data.

The diverter 400, first chamber 340, first partition 338, and second partition 212 are configured to allow fluid to flow through the first chamber 340 and around the first and second sensor probes 384, 388 along a simple flow path (fluid passage 446) that does not promote turbulent fluid flow nor generation of air bubbles. In some examples, either of the first or second partition 338, 312 may include a different profile to minimize turbulence. In other examples, the diverter and chamber inlets 404, 354, first and second ports 408, 608, and chamber and diverter outlets 356, 606 associated with the diverter 400 may be configured or otherwise shaped to promote laminar flow into and from the first chamber 340.

For example, the diverter inlet 404 may include a mouth formed in the inner surface 456 and body 454 of the second housing 350 just upstream of an inlet side of the diverter 400. Such a mouth, as defined by the inner surface 456 and the body 454 of the second housing 350, may widen and deepen along a direction from a starting point and moving toward the diverter 400. In another example, a similar structure may be formed as part of the diverter outlet 604 except that structure will be wider and deeper at starting point (the diverter outlet) than at an endpoint downstream of the diverter.

A chamber that is isolated from a main flow of fluid through a conduit of a fluid system, such as the first chamber 340, allows for reduction of turbulence, bubbles, and debris circulating on or near probes, such as the first and second probes 384, 388 illustrated in FIGS. 3A and 3B. Reduction in such operating conditions can promote accurate sensing of, for example, chemistry-related parameters for the fluid being tested. For the same objective of minimizing turbulence, in other examples, the first chamber 340 may include one or more baffle-like structures extending from a surface of the first housing 330, the second housing 350, and/or the first cover 210. Such baffles may slow down and impact the turbulence of fluid flowing through the first chamber 340. In addition, the first chamber 340 may include a user serviceable (or non-serviceable) filter medium that may keep debris from reaching the probes. The first chamber 340 may also include a plug that can be used to drain the first chamber 340.

Air bubbles can cause sensors like pH sensors, to produce erroneous data. In such a situation, a pH sensor may report readings that are outside of an expected range values or fluctuate relative to one another more than an expected standard deviation. Such readings may be completely unusable to determine even a range for the actual pH of a fluid. This problem is further compounded by the fact that the amount of time an air bubble(s) may persist on the surface of a probe for example, in completely unpredictable. Furthermore, in the case of pH sensors, probes cannot be treated with widely used types of coatings (e.g., xylene which can make water bead or flow and accumulate) to mitigate this issue because such probes are often constructed of hydronium glass and are very sensitive.

One way to avoid air bubbles is to minimize the types of flow patterns (e.g., turbulent, non-laminar) that increase the likelihood of bubbles forming within the fluid as it flows. The size and configuration of the following combination of features are effective in accomplishing this objective: (1) the arrangement of the diverter and chamber inlets 404, 354, first and second ports 408, 608, and chamber and diverter outlets 356, 604; (2) the simple flow path provided by the fluid passage 446 defined within the first chamber 340 by the (a) first and second partitions 338, 312, and (b) walls of the first cover 210 and the first housing 330 of the chassis 300; and (3) the configuration of the protruding wall 402 of the diverter 400 as located within a main flow of fluid through the sensor assembly 200. In addition, other examples discussed below with reference to FIG. 11, may incorporate a control scheme involving operation of other components in a fluid system in communication with control components of the sensor assembly 200 to address air bubbles.

FIG. 4 illustrates a printed circuit board 490 ("PCB 490"), antennas 492, and portions of the first and second sensors 382, 386 disposed within the second chamber 380. In one example, components of a SACS for the sensor assembly 200, including the PCB 490 and antennas 492, as well as the first and second sensors 382, 386, may be electrically isolated. As discussed below, this design feature has particular utility where one of the sensors is a pH sensor.

With pH sensors, a signal between a reference electrode and ground is being measured. In fluid systems where the sensor assembly 200 may be employed, such as the fluid system 50 of FIG. 1, the panel 198, a control box that differs in some way from the panel 198, or a RS485 cable from either, may be connected to the sensor assembly 200 and earth-grounded. The reference electrode of the pH sensor may carry a minimum voltage. However, if it is not isolated, and then forced to ground while connected to at least one other component also connected to ground, the reference electrode will have no reference to its ground and be faulty.

As a result of the reference electrode being faulty, the pH values detected by that pH sensor will also be faulty. Further, a component downstream of the sensor assembly, such as the chlorinator 194, may produce a wide range of electrical signals and operate on its own electrical loop at a much higher voltage. Absent the incorporated electrical isolation of the sensor assembly 200, the sensor assembly 200 may be exposed to the much higher (or lower voltages) because there is no reference it can recognize. Accordingly, sensors and other control components of the SACS (e.g., PCB(s), antenna(s), memory and storage device(s), etc.) incorporated in the sensor assemblies according to the present disclosure are electrically isolated so that regardless of any external connections, these components are isolated and operate as expected.

In addition to electrically isolating various components as previously discussed, sensor assemblies according to the present disclosure may include additional isolation circuity based on the types of sensors provided for the first and second sensors 382, 386. For example, for a combination of a pH sensor and an ORP sensor or a salinity sensor, operation of the non-pH sensor may cause an increase in impedance in a circuit that impacts an ability of the pH sensor to measure pH accurately or entirely. Conversely, operation of the pH sensor may impact the accuracy of an ORP sensor provided as the non-pH sensor. As a result, sensor assemblies according to the present disclosure may incorporate an opto-isolator to control staging of when pH and ORP or salinity are measured.

In addition to components disposed in the first and/or second chamber 340, 380 already discussed, a SACS of a sensor assembly according to the present disclosure may include additional control system components. For example, the sensor assembly 200 may include a flow sensor 494 for detecting a flow rate of a main flow of fluid through the sensor assembly 200. As shown in FIG. 4, the second housing 350 may include a connector 458 configured to receive and secure the flow sensor 494 to the chassis 300. The connector 458 may protrude from the outer surface 452 and define an aperture surrounded by some type of interlocking structure, such as a threaded wall as shown, with the aperture extending through the body 454 to the inner surface 456 of the second housing 350. It will be understood that the chassis 300 may include multiple connectors 458 to accommodate additional sensors (e.g., temperature, salinity, etc.).

Additional components such as data and power connection terminals, solid state components, memory and various types of data storage devices may be housed within the second chamber 380. Furthermore, all the electronics required to interface with at least the first and second sensors 382, 386 may be packaged within the same body. In one example, the PCB 490 may be part of a single SACS package that includes a microcontroller, a communication device (e.g., NFC, WIFI, BLUETOOTH, ZIGBEE, or the like), LED indicators, and an LCD or other type of visual display. The SACS package may be removably installed in the second chamber 380 by attachment to the chassis 300 and/or the second cover 220.

The sensor assembly 200 may be equipped with further additional sensors. For example, a flow sensing wheel may be provided within the first chamber 340 to measure flow rate. The first chamber 340 may also be equipped with a flow switch that can indicate if a flow of fluid is present. In still other examples, the first chamber 340 may be equipped with sensors for measuring salinity and pressure. A sensor assembly controller of a SACS for a sensor assembly according to the present disclosure, may be configured to operate or cause operations of different components of the sensor assembly and non-sensor assembly components in a fluid system, based on information from one or more of the sensors of the sensor assembly. An exemplary sensor assembly controller 1160 is illustrated schematically in, and discussed with reference to, FIG. 11.

Figure 5:
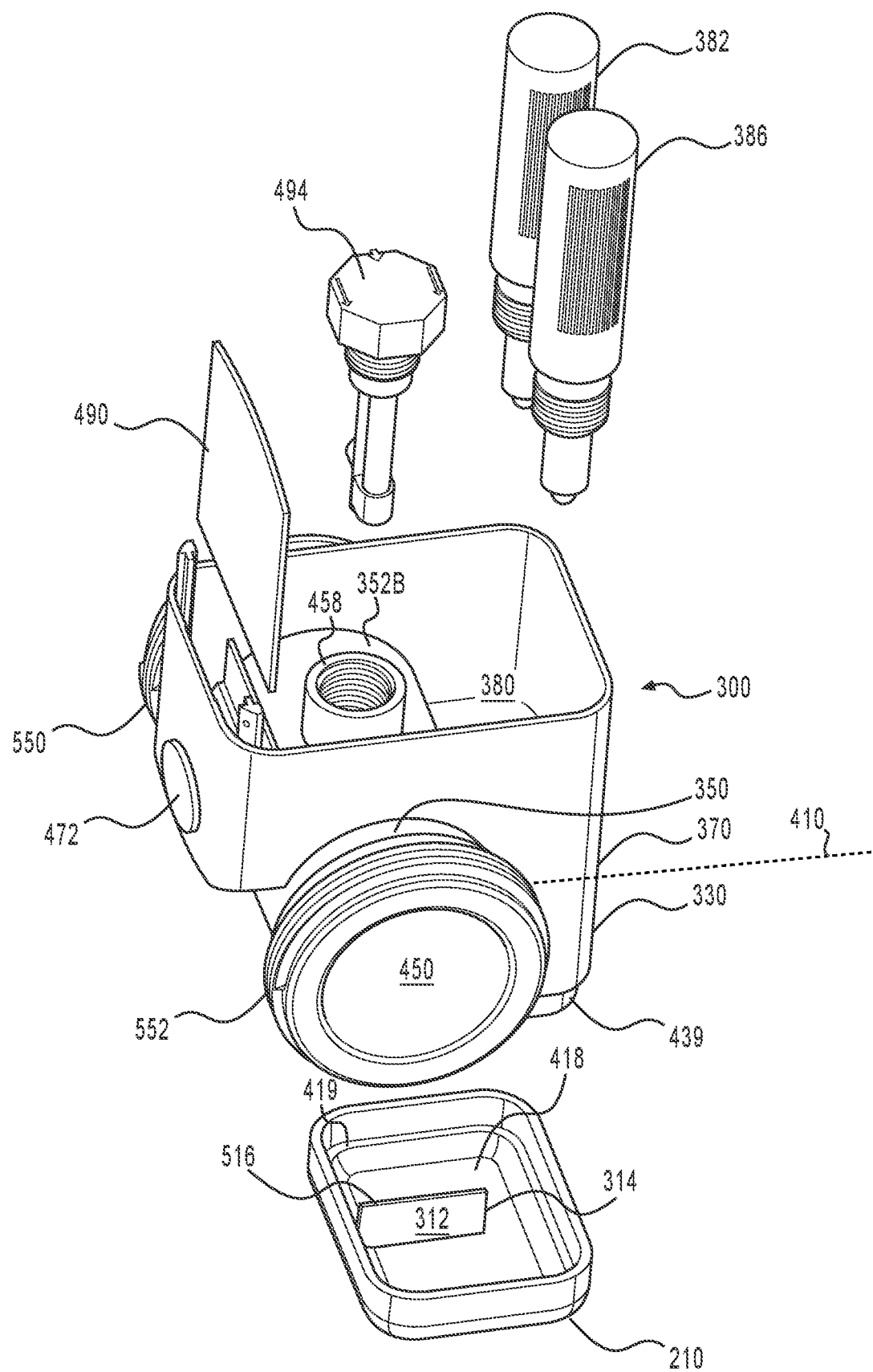
FIG. 5 illustrates an exploded view of exemplary sensor assembly components, according to an aspect of the present disclosure.

FIG. 5 illustrates an exploded view of certain sensor assembly components according to the present disclosure. The chassis 300, the first cover 210, the first and second sensors 382, 386, and the flow sensor 494 are shown in FIG. 5 and reveal various structural features that further make clear the utility and capabilities of the chassis 300. For example, along the first and second adapters 206, 208 (see FIGS. 2-3B), first and second fittings 550, 552 provide for simple and rapid processes for installing and removing the second assembly 200, in total, from a fluid system. Furthermore, certain aspects of the chassis 300 discussed below enable rapid and uncomplicated procedures for accessing and repairing or replacing critical components such as the first and second sensors 382, 386, as well as for maintaining the first chamber 340.

Upon removing the second cover 220, each of the PCB 490, the first and second sensors 382, 386, and the flow sensor 494 will be accessible for inspection. In some examples, the chassis 300 may be equipped with terminals that correspond to plugs or connectors of the PCB 490. Thus, in situations where it may be more advantageous to repair or replace the PCB 490 instead of replacing an entire sensor assembly (e.g., new sensors recently installed, first chamber recently serviced, assembly installed in tight space with restricted access), the PCB 490 may be disconnected and removed for inspection and testing. Further, a repaired or replacement PCB may be readily reinserted and operatively connected to the chassis 300.

Turning to the first, second, and flow sensors 382, 386, 494, each sensor may be disengaged from a respective aperture or connector and removed through the second chamber 380. More specifically with respect to the chassis 300 of FIG. 5, any of these sensors may be rotated until a threaded surface is longer engaged to a corresponding threaded surface of a respective aperture or connector. The sensors may just as easily be reinstalled in the chassis 300 if positioned in a respective aperture or connector and rotated in an opposite direction.

Accordingly, if a user observes or suspects a sensor is mal-functioning or is alerted that an operating life of one or more sensors has expired, the second cover 220 may be quickly removed and the sensor in question may be readily inspected and/or replaced. This interchangeability enabled by the chassis 300 is particularly advantageous for sensor assemblies that include sensors (probes) that need to be replaced on a regular basis (e.g., yearly), such as pH sensors, for example.

Sensor assemblies of the present disclosure are mechanically designed to provide a high degree of sensor serviceability — accessing and servicing or replacing one or more sensors are matters of routine maintenance that are neither labor intensive nor time-consuming. This serviceability coupled with the packaged SACS which may include the PCB 490 tracking sensor operating life and performance, enables implementation of a wide range of data and performance-based procedures that may improve the overall performance of a fluid system and/or operating lives of sensor assemblies and/or different fluid system components. For example, with a SACS, a sensor assembly according to the present disclosure may (1) track the operating life of a pH sensor, for example, and (2) be configured to (a) require, (b) issue an alert requiring, (c) suspend operation until, or (d) control a fluid system to require-replacement of the sensor.

Requiring regular replacement of sensors may drive an industry practice to produce inexpensive sensors that have a relatively short operating life. In turn, regular sensor replacement could result in measured parameters for a fluid system and its components being more accurate more of the time over an operating life of the fluid system. In addition, causing users/fluid system operators to institute a practice of regular sensor replacement could result in fewer situations where component replacement is forgotten about or otherwise neglected due to extended time-periods between component servicing/replacement. Further, providing regular sensor replacements may ensure that certain conditions that may result in damage to one or more fluid system components almost never go un-recognized. As a result, regular sensor replacement in the sensor assemblies according to the present disclosure could reduce the chances that other fluid system components stop working before expected.

A time when one or more sensors are replaced may also be an opportune time to utilize the first cover 210 to service the first chamber 340 of the sensor assembly 200. As can be seen in FIGS. 3A, 4, and 5, the first housing 330 of the chassis 300 may include the lip 439 that corresponds, and can be fitted, to the stepped wall 419 of the first cover 210. In some examples, placement of the first cover 210 onto the first housing 330, without more, results in a close fit between the stepped wall 419 and the lip 439 that seals the first chamber 340 from an external area surrounding the sensor assembly 200. In such examples where the first cover 210 is not attached to the chassis 300 by some type of adhesive, the first cover 210 may be removable from the first housing 330, either by hand or with use of a tool. Upon removing the first cover 210, the walls 332, 334, 336, first partition 338, and portions of the fluid passage 446, such as the chamber inlet and outlet 354, 356 and the first and second ports 408, 608, will be accessible for inspection, debris removal, and general cleaning. Accordingly, any blockages or residue that may affect flow of fluid within the first chamber 340 may be removed and optimal flow conditions restored.

FIG. 6A illustrates an overhead view of the chassis 300, and FIG. 6B is a sectional view of the chassis 300 taken from a plane indicated by line 6B-6B in FIG. 6A. The chassis 300 provides a central structural element of a sensor assembly according to the present disclosure and enables substantially all functionalities of that sensor assembly.

In one aspect, the diverter 400 is built into the chassis 300. The chassis 300 therefore provides a compact sampling system that is directly in a flow of fluid as it flows through a fluid system. This substantially eliminates any opportunity for a tested portion of fluid to be contaminated or altered in any way from its composition prior to flowing through the sensor assembly. More succinctly, a fluid being tested is the fluid flowing through the fluid system. Accordingly, values for the parameters measured by the sensor assembly are representative of the fluid in the fluid system.

In another aspect, the first and second housings 330, 350 of the chassis 300 define a substantial portion of the first chamber 340 and the fluid passage 446 which directs fluid from the diverter 400, past the probes 384, 388, and out of the first chamber 340 through diverter outlet 604. Furthermore, absent the first cover 210, the first housing 330 defines and open chamber 640 as designated in FIG. 6B.

The chassis 300 defines a base component to which all other components of the sensor assembly may be attached. Where the chassis 300 includes the first and second fittings 550, 552, the chassis 300 thereby provides a primary mechanical feature for installing a respective sensor assembly in a fluid system. Once installed, the second housing 350 of the housing provides a section of a conduit carrying a main flow of fluid that is conveyed through a fluid system. The chassis 300, via the second housing 350, providing a mechanism for attaching the sensor assembly to a fluid system while having a simple configuration enables easy and rapid replacement of the entire sensor assembly with a spacer. Such a spacer, including a spacer body 710 and first and second fittings 712, 714 on opposite ends of the spacer body 710, is shown in FIG. 7 and discussed below.

Figure 7:
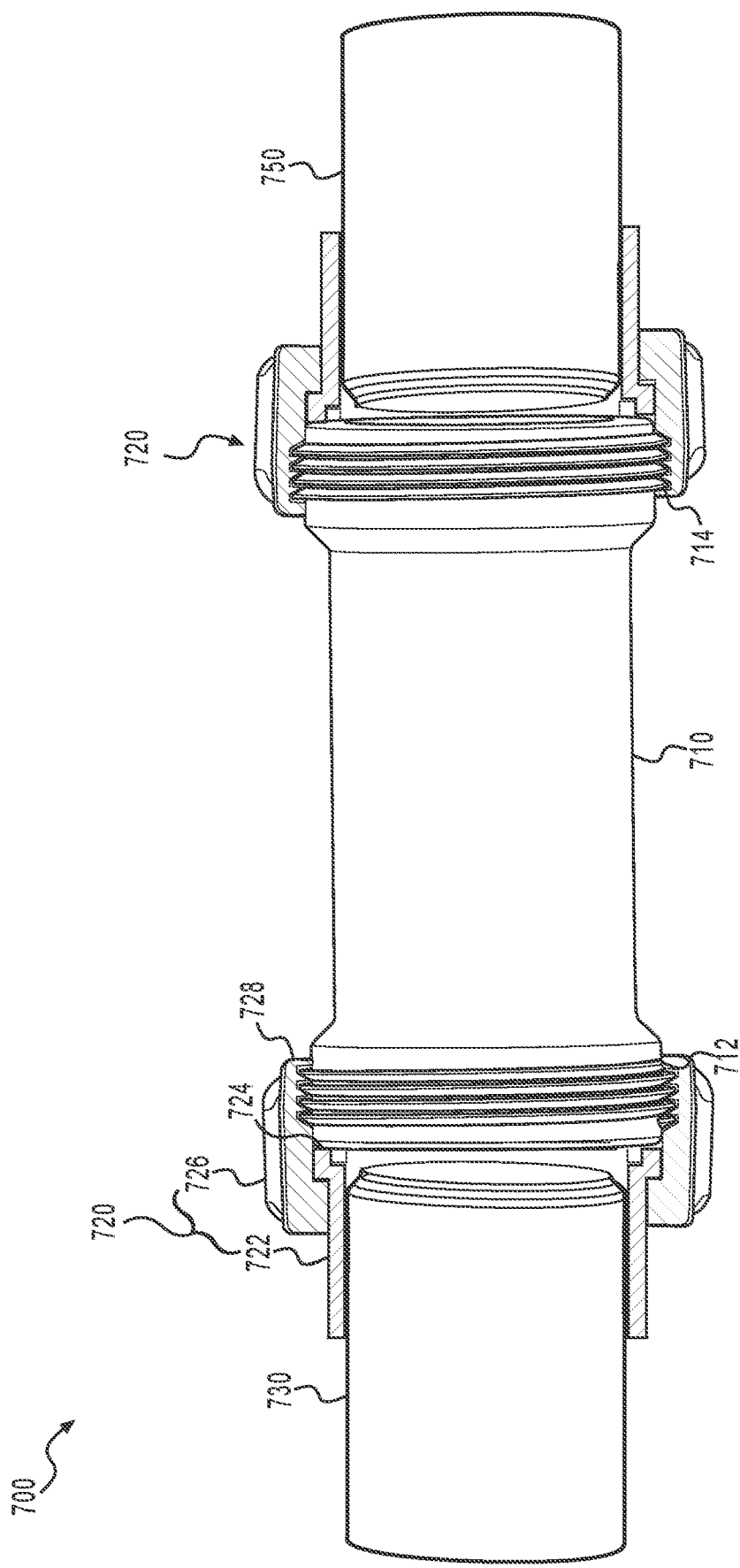
FIG. 7 is an overhead view of a spacer with sectional views of adapters, according to an aspect of the present disclosure.

FIG. 7 is an overhead view of a spacer 700 with sectional views of adapters 720, according to an aspect of the present disclosure. FIG. 7 is intended to illustrate how a chasses according to the present disclosure, such as the second housing 350 of the chassis 400, can be replicated in the form of the spacer 700 and in turn be used entirely in place of a sensor assembly according to the present disclosure. The spacer 700 essentially has utility as a placeholder for a sensor assembly when a fluid system is newly installed, or when the sensor assembly needs to be serviced, taken out of service for an extended period of time (e.g., winterization), or replaced.

FIG. 7 is representative of an installation site for a sensor assembly prior to installation or during periods when a sensor assembly is taken out of service for some type of maintenance or as part of a winterization procedure. Installation and removal processes are described below. For each process, it may be assumed that a flow of fluid being conveyed from the first conduit 730 or the second conduit 750 has been addressed substantially prior to installation or removal process.

Installation of the spacer 700, and a sensor assembly such as sensor assembly 200, may include: sliding a collar 722 of one adapter 720 over a first conduit 730; sliding a collar 722 of another adapter 720 over a second conduit 750; pushing a fastening ring 726 of each adapter 720 toward a distal end of a respective collar 722 so that a ring end 728 is substantially spatially adjacent to a respective collar end 724 along a longitudinal axis of a respective one of the first and second conduit 730, 750; positioning and holding the spacer 700 between the ring ends 728; engaging a leading thread of the first fitting 712 of the spacer 700 with the ring end 728 of the fastening ring 720 for the adapter 720 on the first conduit 730; rotating the fastening ring 726 relative to the first conduit 730, the collar 722, and the spacer 700; engaging a leading thread of the second fitting 714 of the spacer 700 with ring end 728 of the fastening ring 726 for the adapter 720 on the second conduit 750; and rotating that fastening ring 726 relative to the second conduit 750, the collar 722, and the spacer 700.

Engaging the leading threads of either of the first or second fittings 712, 714 may include moving the first fitting 712, for example, into the ring end 728 of the adapter 720 positioned on the first conduit 450. Alternatively, the fastening ring 726 could be slid on the collar 722 toward the first fitting for engagement.

Removal of the spacer 700 or sensor assemblies according the present disclosure may include essentially the installation process in reverse. This may start with rotating the fastening rings 726 in respective directions to eventually disengage each fastening ring 726 from the threads of a respective one of the first and second fittings 550, 552. Once both fastening rings 726 are disengaged, the spacer 700 in the case of FIG. 7, or a sensor assembly, as may be installed, may be moved from in between the first and second conduits 730, 750.

In practice, physical installation and removal of a sensor assembly, such as sensor assembly 400, will require the same simple processes as discussed above for the spacer 700. Furthermore, these simple processes can be used to readily swap the spacer 700 in and out for the sensor assembly 400 within sections of a fluid system such as the installation site between the first and second conduits 730, 750 illustrated in FIG. 7. As a result, servicing that requires removal, replacement, or reinstallation of the sensor assembly, can be accomplished using the spacer 700 at scheduled times or on an ad-hoc basis with few constraints. Further, the processes previously described may be carried out without: prolonged fluid system downtime; significant costs; having to perform complex procedures; or having to find and use skilled labor or special tools.

Examples of when the installation and removal processes discussed above may be used specifically to swap a spacer for a sensor assembly and vice versa, include situations involving an initial installation of a fluid system and when a fluid system needs to be winterized. Each situation provides uniquely different issues that could result in damage to the sensors of a sensor assembly.

In the case of a new fluid system installation, when a new system is initially goes online (i.e., is turned on or conveys fluid there through for the first time), there may be various elements, such as debris, foreign liquids, tools, hardware, etc., within various conduits of fluid system resulting from its recent construction. Exposing fluid sensors, e.g., pH, ORP, alkalinity, or the like, to such elements can the accuracy of the readings produced by those sensors. Significant damage to the point of rendering one or more sensors unusable is also very possible or even probable.

In addition to these risks, when a new fluid system initially goes on line, there may be little need to measure the parameters of pH, ORP, salinity, and others discussed herein. Rather, objectives during this phase of fluid system installation are often to ensure fluid is conveyed entirely through the system and any unwanted elements are flushed out. Given the ease with which a sensor assembly according the present disclosure can be swamped for a spacer 700, having the spacer 700 installed during new fluid system installation provides several advantages over other installation processes where a component of a fluid system is not substituted for. First, the spacer 700 can be installed when conduit is first being run in the construction of the fluid system. There is no need to have to cut and replaced any portion of conduit already installed. The spacer 700 maybe installed on the conduit just as any other fitting (e.g., 90° elbow, joint, tee) would be for an initial install. Furthermore, with the spacer 700 in place when the new fluid system goes online, there is no chance of any sensors of a to-be-installed sensor assembly being damaged due to debris or other elements being carried with a fluid flowing within the system at that time.

In a situation where a fluid system needs to be winterized, the spacer 700 may be installed in place of the sensor assembly 200, for example. This is particularly advantageous for maintaining proper operation and realizing an expected operating life of many sensors. As discussed in more detail with reference to FIG. 8, many sensors that are used to measure parameters discussed herein include probes that must be maintained within a fluid (must be "wet") at all times. If these probes become dry, they may not function correctly, may not provide accurate readings, or at minimum may have to be submerged in fluid for a prescribed (often long) period of time before they can be used again. However, if the fluid in which some of the probes are kept freezes, similar damage or functional limitations may result.

The capability of being able to readily remove a sensor assembly and install the spacer 700 as previously discussed can be used to effectively address issues brought on by winterization requirements. This capability allows a user or system operator to store the sensor assembly filled with sufficient fluid for the probes in a location where the fluid will not be susceptible to freezing. Further, it allows the user to readily put the sensor assembly back into service when environmental temperatures rise to acceptable levels. In addition to this physical capability of removal and reinstallation, sensor assemblies according to the present disclosure may be equipped with multiple temperature sensors that may be used to alert a user that a winterization procedure needs to be implemented. As discussed with reference to FIG. 11, a sensor assembly according to the present disclosure may be equipped with a SACS and a temperature sensor that detects an ambient temperature where a sensor assembly is installed, as well as a sensor for detecting the temperature of fluid within a second housing or a first chamber.

Some fluid systems, such as many "sense and dispense" types of systems, typically implemented in commercial settings, may require first and second conduits be attached to a sensing type of device, and cut or plumbed into a main fluid pipe or conduit separately upstream and downstream of a fluid system component. This process may be time-consuming, require special tools and labor, and be costly. In contrast, with an "on-the-pipe" feature, which is illustrated in FIGS. 2, 3A, and 3B, as well as FIG. 7, a portion of a fluid system that is dedicated to determining concentrations of various chemicals and includes a sensor assembly according to the present disclosure, need not be complicated, large, or require expertise for installation and maintenance. Thus, sensor assemblies and spacers of the present disclosure may be implemented in, for example, commercial or residential pool and/or spa fluid systems.

Figure 8:
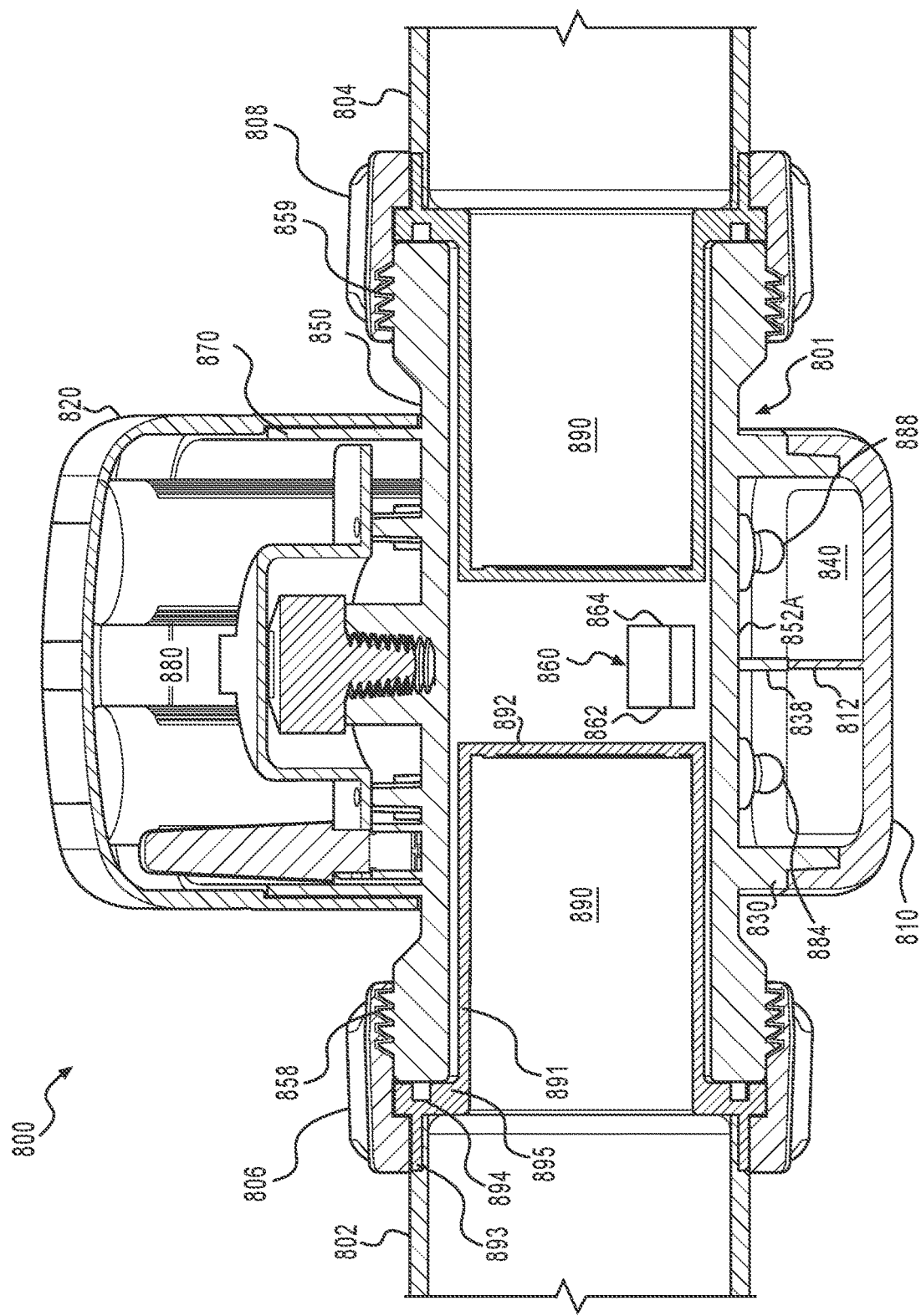
FIG. 8 is a sectional view of an exemplary sensor assembly according to an aspect of the present disclosure.

FIG. 8 is a sectional view of exemplary sensor assembly 800 according to an aspect of the present disclosure. FIG. 8 illustrates how the sensor assembly 800 may be sold or stored using caps 890 that are secured to and within a second housing 850 of a chassis 801 by first and second adapters 806, 808. Each cap 890 includes a collar 893, flange 895, and an O-ring 894 for engaging and sealing against a respective adapter 806, 808. A drum 891 of the cap 890 extends to an end face 892 so that: (1) the end faces 892 are positioned adjacent to a respective one of a diverter inlet 862 or a diverter outlet 864; and (2) a substantial space defined within the second housing 850 is filled by the drums 891 of the caps 890.

Whether the sensor assembly 800 is new or being stored, a first chamber 840 can be substantially filled with a fluid that preserves first and second probes 884, 888 in a wet state and remains within the sensor assembly 800 until the caps 890 are removed. As a result, sensors may be calibrated prior to installation in the sensor assembly 800 and preserved in a wet and calibrated state from the time of manufacture until installation. In turn, installation in the field of the sensor assembly can be as simple as a plug and play type of process. More specifically, a first chamber 840 may have probes that are preinstalled in a factory and calibration values may be pre-stored in a memory of a SACS for the sensor assembly 800. The sensor assembly 800 may be shipped to include the caps 890 which hold a buffer solution (such as 3 M KCL) in the first chamber 840 to allow for the probes 884, 888 to be in a wet environment and prevent drying.

Figure 9A:
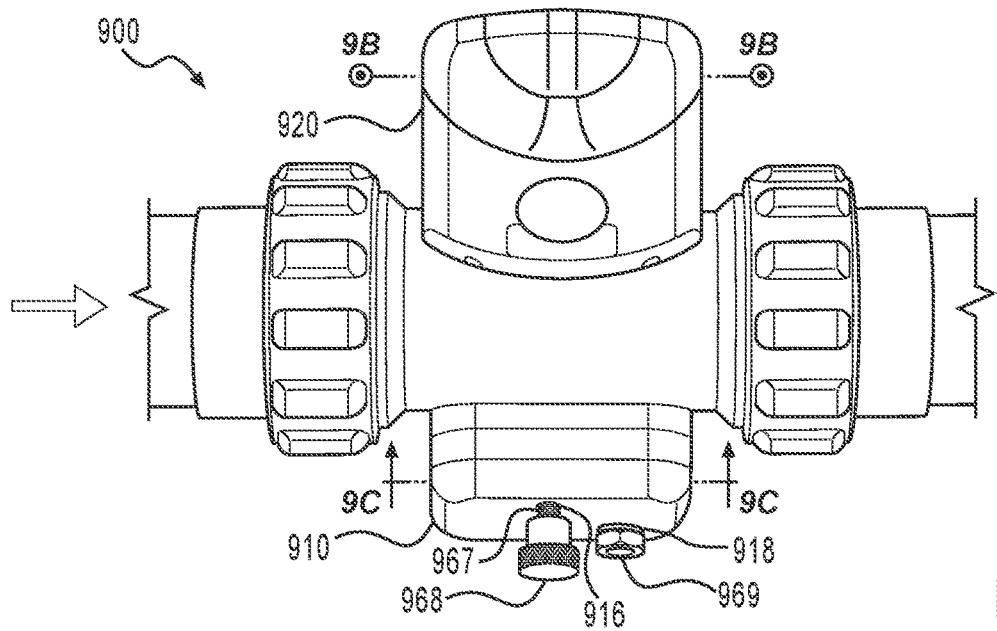
FIG. 9A illustrates a front perspective view of an exemplary sensor assembly according to an aspect of the present disclosure.
Figure 9B:
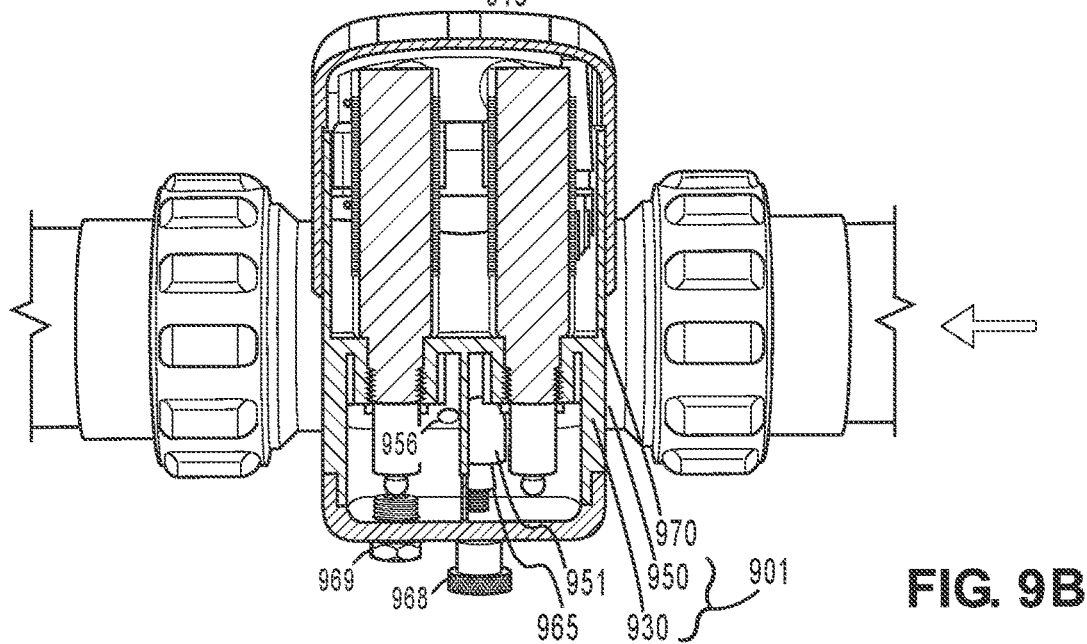
FIG. 9B is a sectional view of the sensor assembly of FIG. 9A taken from a distal plane looking out of the page as indicated by line 9B-9B.
Figure 9C:
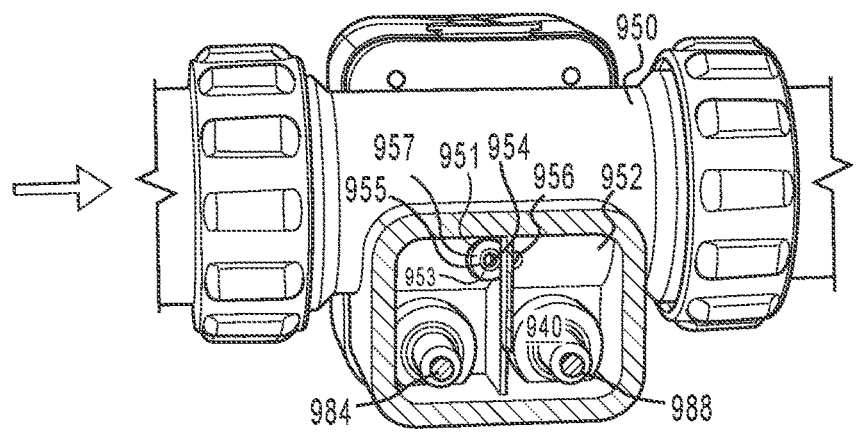
FIG. 9C is a sectional view of the sensor assembly of FIG. 9A taken from a plane indicated by line 9C-9C.

FIG. 9A illustrates a front perspective view of an exemplary sensor assembly 900 according to an aspect of the present disclosure. FIGS. 9B and 9C are sectional views of the sensor assembly 900 of FIG. 9A taken from planes indicated by lines 9B-9B and 9C-9C, respectively.

The sensor assembly 900 includes a chassis 901, a first cover 910 and a second cover 920. As illustrated in FIG. 9B, the chassis 901 includes first, second, and third housings 930, 950, 970. Along with the first cover 910, the first housing 930 defines a first chamber 940 in which sensor probes 984, 988 may be positioned and exposed to a portion of a fluid flowing through the sensor assembly 900.

The first cover 910 includes a first aperture 916 configured to receive a shaft 967 of a valve 955, 965, 967, 968 and a second aperture 918 configured to receive a plug 969. As shown in FIG. 9B, the valve includes a knob 968 on one end of the shaft 967 and a valve member 965 on an opposite end. By movement of the shaft 967, the valve member 965 may engage or disengage a valve port 951 that extends from an outer surface 952 of the second housing 950 of the chassis 901. The valve port 951 extends from the outer surface 952 to a respective end face 957 and defines a valve seat 953 that includes an opening 955 formed in the end face 957. The opening 955 is configured to receive an end of the valve member 965, and the valve seat 953 is configured to engage the end of the valve member 965. The end of the valve member 965 may engage the valve seat 953 to such a degree that the chamber inlet 954 is not in fluid communication with the opening 955 and thus not in fluid communication with the first chamber 940.

In one example, both the plug 969 and the valve 955, 965, 967, 968 may be hand operated and move within the first chamber 940 and relative to the first cover 910. The plug 969 may be turned or otherwise moved to disengage the second aperture 918, which may then be in an open state and used to the drain the first chamber 940 of fluid. The knob 968 may be used to easily change the position of the valve member 965 in relation to the chamber inlet 954 such that it can be utilized by a user to adjustably control an amount of flow of fluid into the first chamber 940.

More specifically, the knob 968 may be turned or otherwise moved such that the knob 968 moves towards or away from an outer surface of the first cover 910 and the valve member 965 likewise moves towards or away from a valve port 951. In one example, the knob 968 may be turned counterclockwise and cause the shaft 967 to move outward through the first cover 910 and the valve member 965 to disengage or otherwise move away from a valve port 951. Rotation of the knob 968, by hand in some examples, in the opposite direction will cause the opposite movement of the valve member 965 towards the valve port 951. The rotation and corresponding movement may continue until the end of the valve member 965 is fully engaged with the valve seat 955, thereby discontinuing fluid communication between the chamber inlet 954 and the first chamber 940.

Figure 10:
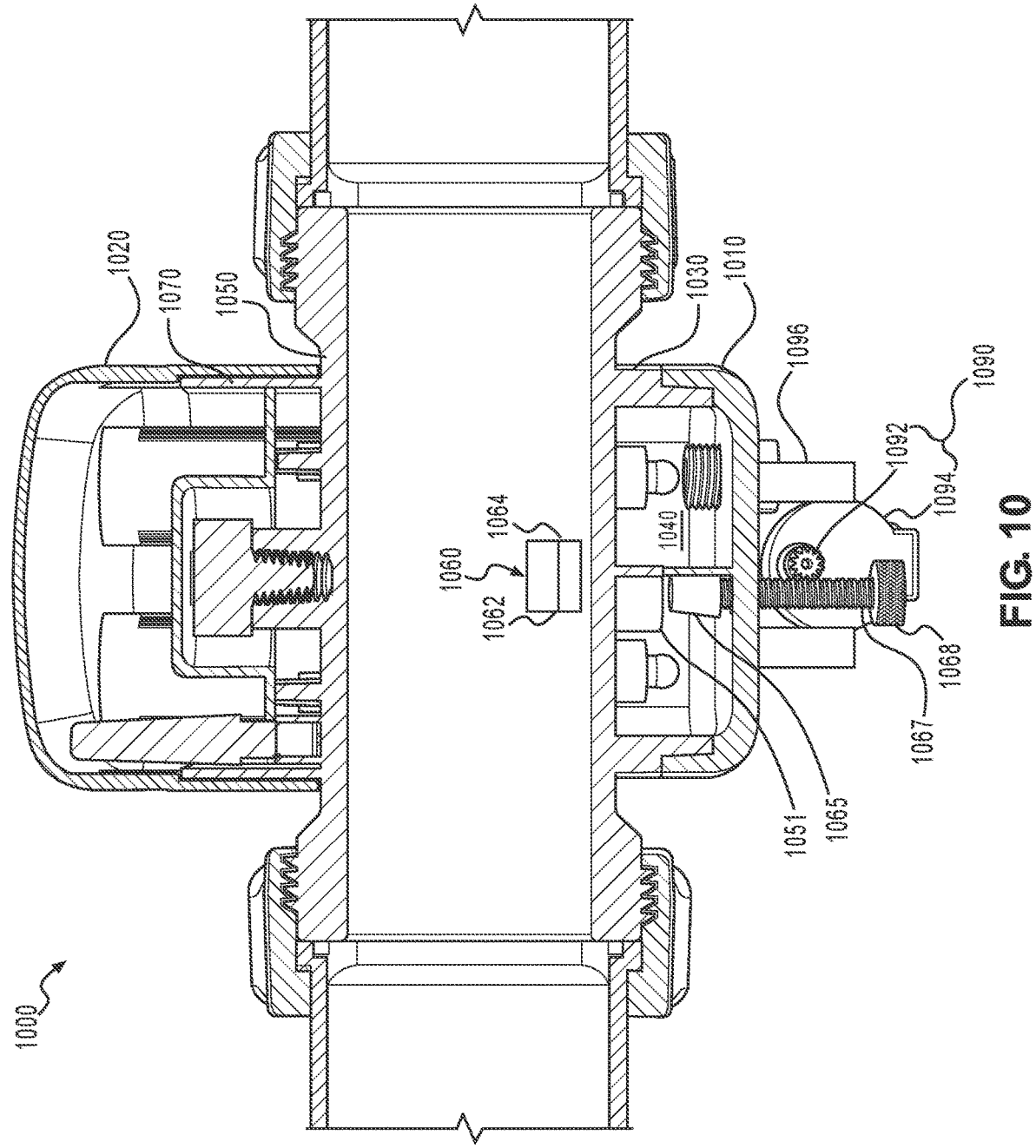
FIG. 10 is a sectional view of an exemplary sensor assembly according to an aspect of the present disclosure.

FIG. 10 is a sectional view of an exemplary sensor assembly 1000 according to an aspect of the present disclosure. Like other exemplary sensor assemblies discussed herein, the sensor assembly 1000 of FIG. 10 includes a chassis with first, second, and third housings 1030, 1050, 1070, a first cover 1010, and a second cover 1020. The chassis provides a diverter 1060 including a diverter inlet 1062 and a diverter outlet 1064 configured to be in fluid communication with a first chamber 1040 in which sensors are disposed.

Like the sensor assembly 900 illustrated in FIGS. 9A-9C, the chassis for the sensor assembly 1000 includes a valve port 1051 configured to receive a valve member 1065 that is attached to a shaft 1067. The shaft 1067 extends through a wall of the first cover 1010 to a knob 1068 outside of the first chamber 1040. Operation of an actuator 1090 may be used to control fluid communication between the diverter inlet 1062 and the first chamber 1040.

More specifically, the shaft 1067 may be engaged to a gear 1092 of the valve actuator 1090 that is rotated via attachment to a drive shaft of a motor disposed within a housing 1094. As shown in FIG. 10, the housing 1094 may be mounted to the first cover 1010 by supports 1096. In one example, the valve actuator 1090 may be removably attached to the supports 1096. With the actuator 1090 removed, or if the actuator does not prohibit movement of the gear 1092 when it is not in operation, the shaft 1067 may also be moved by hand in some examples.

With the valve actuator 1090, the sensor assembly 1000 provides a stand-alone or additional mode of controlling fluid flow into the first chamber 1040. In one example, a SACS for the sensor assembly 1000, such as SACS 1150 discussed with reference to FIG. 11, may be configured to control operations of the valve actuator 1090. Such a SACS may implement operation of the valve actuator 1090 in response to any of operational conditions previously discussed.

For example, if readings from one or more sensors are outside of a normal range, an increase in turbulence may be recognized by the sensor assembly 1000, via a SACS, as a potential cause of the abnormal data. In some examples, this determination may be confirmed by polling a flow sensor and operating the valve actuator 1090 to move the valve member 1065 towards a chamber inlet (not shown) to reduce flow into the first chamber 1040. In one example, based on the flowrate detected by the flow sensor, the valve member 1065 may be moved to a location associated with a known degree of chamber inlet restriction. In other examples in which a flow sensor is not polled, the position of the valve member 1065 may be changed concurrently with a polling of a sensor that provided the abnormal readings until: (A) the readings fall within an expected range; (B) a certain period of time has elapsed; or (C) the valve member 1065 has restricted the chamber inlet to such a degree that turbulent flow would not be possible and therefore not the cause of the abnormal readings from the sensor.

In addition to controlling the valve actuator 1090, the sensor assembly 1000 may control, via a SACS (discussed in more detail with respect to FIG. 11), other fluid system components such as a pump, chlorinator, and/or acid dispenser. Control of the valve actuator 1090 may be combined with control of one of these other components in response to conditions described herein such as abnormal data being produced from one or more sensors. In one example, a pump and the valve actuator 1090 may be controlled in tandem to address turbulence or air bubble issues.

Figure 11:
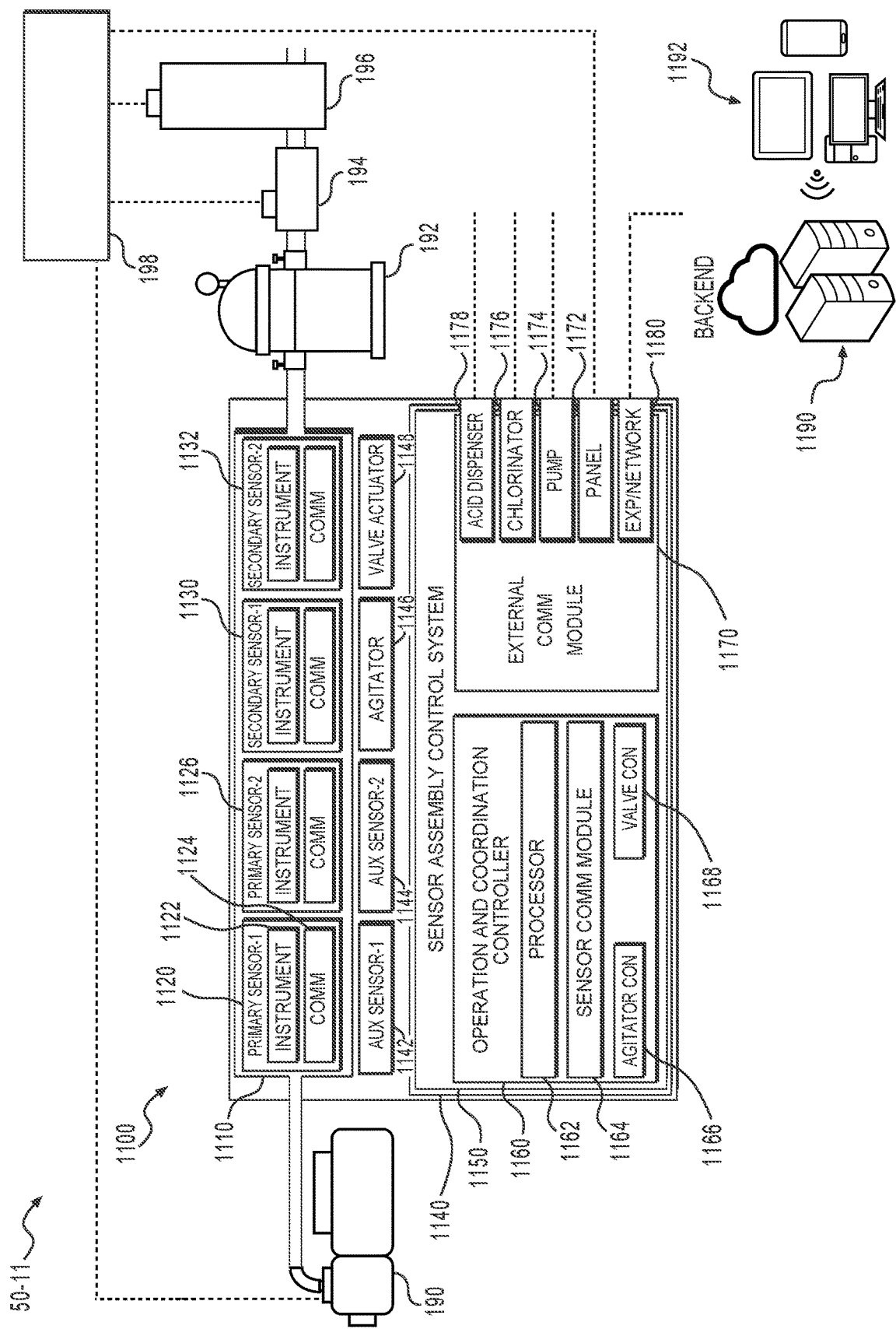
FIG. 11 is an illustration of exemplary system components of a fluid system along with a schematic view of a sensor assembly and sensor assembly control system, according to an aspect of the present disclosure.

FIG. 11 is an illustration of a fluid system 50-11 that includes an exemplary sensor assembly 1100 according to an aspect of the present disclosure. In FIG. 11, the sensor assembly 1100 is illustrated schematically and includes a first chamber 1110, first and second auxiliary sensors 1142, 1146, an agitator 1146, a valve actuator 1148, such as the exemplary valve actuator 1090 of the sensor assembly 1000, and a second chamber 1140. The first chamber 1110 may include first and second primary and secondary sensors 1120, 1126, 1130, 1132 that: may be disposed within and/or attached to the first chamber 1110; and monitor a parameter related to activity within, by, or that affects the first chamber 1110 and/or fluid within the first chamber 1110. Each of the sensors that may be included in the sensor assembly 1100 may include an instrument 1122 (e.g., probe, pitot tube, fiber optic light transmitter, gauge, optical encoder, etc.) for monitoring a respective parameter, and a communications module 1124. The second chamber 1140, on the other hand, includes a sensor assembly control system 1150 ("SACS 1150").

A power input (not shown) may be provided in the sensor assembly 1100 and configured to connect to a power source that services one or more components of the fluid system 50-11. In one example, this power input may provide a low voltage supply (e.g., 24V AC, 12V AC) that will be utilized to provide all the power requirements for the sensor assembly 1100. Hardware that may be incorporated in the sensor assembly 1100 may handle/require/output low voltage signals (e.g., 5V, 12V) and manage power requirements for all devices including primary, secondary, and auxiliary sensors. In another example, some sensors, such as the first and second primary sensors 1120, 1126 may include their own power source such as a battery.

The first and second primary sensors 1120, 1126 may correspond to sensors that are secured to a chassis by first and second apertures (e.g., chassis 300 and first and second apertures 342, 344), and include probes or other types of instrumentalities that extend into the first chamber 1110. In one example, the first and second primary sensors 1120, 1126 may detect a combination of fluid properties from a group including pH, ORP, salinity, alkalinity, dissolved oxygen, water hardness, nitrates, calcium, etc.

The first and second secondary sensors 1130, 1132 may include sensors that monitor flowrate, temperature, presence of fluid, position (e.g., position of a valve shaft), and other properties that indicate a state of operations and/or conditions within and generally with respect to the first chamber 1110. In one example, the first secondary sensor 1130 includes a temperature sensor to detect a temperature of the fluid within first chamber 1110 or a temperature of the first chamber 1110 (if different from the fluid temperature). In another example, the second secondary sensor 1132 may include a flowrate sensor that measures the flowrate of fluid being conveyed through the first chamber 1110. In another example, the second secondary sensor 1132 may be: (1) positioned on a first or second partition (such as first or second partition 338, 312 shown in FIGS. 4); and (2) monitor activity and a parameter related to a boundary layer between laminar and turbulent flow for the fluid in the first chamber 1110 with respect to a surface of a respective partition. In still another example, a flow switch that indicates or reports a flow state via a relay (e.g., an electrical relay) may be provided in the first chamber 1110 as, or in addition to a flowrate sensor provided as, the second secondary sensor 1132.

The first and second auxiliary sensors 1142, 1144 may include sensors that monitor parameters for fluids, devices, or environmental conditions outside of, adjacent to, upstream or downstream of the first chamber 1110 and/or a diverter, such as the diverter 400 in FIG. 4. In one example, the first auxiliary sensor 1142 includes a flowrate sensor, such as the flowrate sensor 494 in FIG. 4, for detecting the flowrate of fluid through a conduit carrying a main flow of through the sensor assembly 1100. In another example, the second auxiliary sensor 1144 may include a temperature sensor that detects the ambient temperature of an area surrounding the sensor assembly 1100 (or at least external to and surrounding the first chamber 1110).

The agitator 1146 may include a device that is configured to tap, vibrate, or otherwise apply a force to, sensors and/or a portion of the sensor assembly 1100 that defines the first chamber 1110 (such as the first cover 210 and/or the first housing 330 of the sensor assembly 400).

The SACS 1150 includes an operation and coordination controller 1160 ("OCC controller 1160) and an external communications module 1170 ("external comms 1170"). In general, the OCC 1160 will be equipped with processing power required to control the sensor assembly 1100. In a specific example, the OCC 1160 may include a microchip processor (e.g., an ATSAMC20) that is selected based on a number of different parameters including memory size (flash/RAM), timer support capabilities, actuator interface compatibility, number of general-purpose Input/Outputs, low voltage operating capabilities, and other factors. As shown, the exemplary OCC 1160 may include at least one processor 1162 and a sensor communications module 1164.

The processor 1162 can implement or otherwise have continuously executing thereon a plurality of services including an operation and data recordation scheduling service, a valve operation service, an agitator operation service, and one or more external device operation services. One such external device operation service may include a pump operation service for directing operations of the pump 190 of the fluid system 50-11 as described below. In one example, each service may be constituted by an application or agent running, or otherwise being implemented on the OCC 1160, that may be part of, or configured to be compatible with, a software product that is installed on or at least partially provided by the SACS 1150 and/or a backend 1190 that operations and information management for the sensor assembly 1100. The software product can provide tools for system management, communication and coordination, estimating and modeling, data conversion and formatting, generating components and/or selectable options of a user interface ("UI"), such as a graphical user interface, supporting selections made through a UI, and any other relevant features.

The OCC 1160 can also include a sensor communications module 1164 ("sensor comms 1164") that interfaces with the processor 1162 and communication modules 1122 for the primary, secondary, and auxiliary sensors 1120, 1126, 1130, 1132, 1142, 1144. Each sensor may transmit data corresponding to a parameter monitored with/by a respective instrument 1124 to the sensor comms 1164. In turn, the sensor comms 1164 may determine an order of priority for sending data to the processor 1162 and send the data according to that order of priority. Alternatively, the processor 1162 may establish the order of priority which the sensor comms 1164 adheres to.

As illustrated in FIG. 11, the OCC 1160 may include an agitator control 1166 that is associated with the agitator 1146, and a valve control 1168 that is associated with the valve actuator 1148. In some examples, either of the agitator control 1166 and valve control 1168 can perform one or more processes to determine or generate an instruction which it transmits to, or otherwise causes an operation specified therein, to be performed by the agitator 1146 or the valve actuator 1148. Accordingly, the agitator and valve controls 1166, 1168 may respectively communicate with and direct operations of the agitator 1146 and the valve actuator 1148, as well as process flow information from any of the sensors of the sensor assembly 1100.

In another example, the agitator and valve controls 1166, 1168 may define control interfaces with the processor 1162, such that instructions may be generated, and control may be implemented at a level of the processor 1162 or a level of the agitator and valve controls 1166, 1168. Instructions may be generated at the level of the processor 1162, and the agitator or valve controls 1166,1168 may direct the agitator 1166 or valve actuator 1168 to perform the specified operations through respective control interfaces. In other situations, control inputs processed by the OCC 1160 may direct operations of one or both of the agitator 1146 and valve actuator 1148 be processed by the agitator or valve control 1166, 1168 and controlled or otherwise implemented by the processor 1162. In another example, the agitator and/or valve control 1166, 1168 may serve merely as a communication channel between the processor 1162 and the agitator 1166 or valve actuator 1168. In still other examples, the agitator control 1166 or the valve control 1168 may be integrated into or otherwise be provided by the processor 1162.

The valve control 1168 may be configured to recognize fully open and fully closed states of a chamber inlet using the valve actuator 1146 and valve components (e.g., shaft, valve member) attached thereto. In one example, the valve control 1168 may be configured to register a signal from an indicator that may be configured to detect or otherwise operate as a way of indicating that the valve actuator 1166 (or valve member) is located in a start (fully closed) or an end (fully open) position. In one example, momentary contact switches, integrated with the valve actuator 1146 or valve components attached thereto, may be used to define, to either the valve control 1168 or the processor 1162: (A) fully open and fully closed states for a chamber inlet; and (B) operation limits for the valve actuator 1148.

In practice, control inputs received through the external comms 1170 may be used, by the processor 1162 or the valve control 1168 (under its own control or through direction by the processor 1162), to control a flowrate of fluid through the first chamber 1110 by operating the valve actuator 1148. In other examples, an operation defined by a control input may be determined to not be possible or one that will negatively affect one or more current operations of the sensor assembly 1100. In this situation, the OCC 1160, via the processor 1162, agitator control 1166, valve control 1168, or combination thereof, may generate, and direct the external comms 1170 to transmit to a source of the control input and/or the panel 198, an indication that the operation will not be performed (and why).

It is through the external comms 1170 that the OCC 1160 may transmit sensor readings, or control outputs (e.g., operational instructions for one or more fluid system components) based on the sensor readings. Communication modules provided with various devices, such as the panel 198, pump 190, chlorinator 194, acid dispenser 196, may communicate with the external comms 1170. In some examples, the external comms 1170 may receive control inputs (e.g., requests for information) that the OCC 1160 processes and may carry out or respond to. For example, a control input from the panel 198 may request a reading from a particular sensor of the sensor assembly 1100 at a time that may differ than a normal reporting cycle for the sensor assembly 1100.

The external comms 1170 can include a first connection terminal, port, or other type of connector 1172 ("first connection 1172") for communication with the panel 198 and/or a service for the panel 198. In addition, the external comms 1170 may include a second connection 1174 for a pump, a third connection 1176 for a chlorinator, a fourth connection 1178 for an acid dispenser, and a fifth connection 1180 for a device configured to connect (wired or wirelessly) to one or more servers of a backend 1190 (e.g., a server) and/or a peripheral device (e.g., a phone, laptop, tablet, personal computer, a controller for an FHD, etc.). Additional connections may be incorporated in the external comms 1170 for other devices such as a sensor assembly other than the sensor assembly 1100 operated by the SACS 1150, storage devices, devices that implement specific communication protocols (e.g., NFC, WIFI, BLUETOOTH, ZIGBEE, or the like) or expand a capability (e.g., increase a number of other devices) of the sensor assembly to communicate with devices using the specific protocol. In another example, the external comms 1170 may be configured to communicate directly with an external device (not shown) that serves as an intermediary between the SACS 1150 and one or more external devices.

In one example, the sensor assembly 1100 may include a temperature sensor for the first secondary sensor 1130, and a temperature sensor for the first or second auxiliary sensor 1142, 1144 for detecting an ambient temperature. The control system 1140 may poll these sensors, determine a differential between the two measured temperatures, and issue an alert to a user or system technician when the ambient temperature falls below a threshold (5° C. for example) and sensor assembly 1100 must be winterized. A probe that may be part of the first or second primary sensor 1120, 1126 and includes a liquid or gel inside of it or is exposed to liquid (or gel) at all times (out of necessity), can be damaged beyond repair if a temperature falls below freezing point. The liquid or gel can expand and ruin the probes, but the above alert may serve as a reminder to have the operator remove the sensor assembly 1100 and install a spacer, such as the spacer 700 of FIG. 7, for the winterization process.

In another example, one of the first or second secondary sensors 1130, 1132 may include a flow sensing wheel provided within the first chamber 1110 and configured to measure an amount of flow therein. Additionally, the first chamber 1110 may be equipped with a flow switch that can indicate to the SACS 1150 if a flow fluid is present. In one example, the flow switch indicates or reports a flow state via a relay (e.g., an electrical relay). If flow is not present, the SACS 1150 may transmit: (1) previous values that were output by the first and second primary and secondary sensors 1120, 1126, 1130, 1132 when a flow was present; (2) a flow rate sensor provided as the first or second auxiliary sensor 1142, 1144 when a flow was present; (3) current values for those sensors; and (4) an indication that a flow is not present. The SACS 1150 may transmit the above information to the panel 198.

In still other examples, the first chamber 1110 may be equipped with sensors for measuring salinity and pressure. In one example, information from a pressure sensor may be used by the SACS 1150 to control the pump 190. In other examples, the SACS 1150 may transmit the pressure, salinity, and/or other parameters (e.g., temperature, flow rate, alkalinity) for fluid flowing in the first chamber 1110 (and a second housing), to the panel 198. Depending on a control scheme and protocol for the fluid system 50-11, the SACS 1150 may include instructions for the panel 198 to carry out with respect to other components, such as the pump 190, the chlorinator 194, and/or the acid dispenser 196. In still other examples, the panel 198 may receive the sensor values from the sensor assembly 1100 and determine what control measures will be implemented with other fluid system components as a result.

As previously mentioned, one issue that is common to fluid property sensors including probes is the issue of bubbles of air sitting on a probe head. This can cause a sensor, such as a pH sensor, to produce erroneous readings. Sensor assemblies according to the present disclosure may be configured to actively address such an air bubble issue in a series of processes that include determining the presence of a bubble is likely and creating conditions that promote movement of the air bubble from the head of a probe.

Regarding a recognition process, determining an air bubble(s) is present on the probe can include recognizing that readings for the corresponding sensor for the probe have gone well outside and expected range of values. Regarding a remediation process, the sensor assembly 1100 may implement processes to affect fluid flow around a probe to encourage an air bubble to move from a probe head. To promote this movement, the sensor assembly 1100 may control: (1) a respective sub-component, such as the agitator 1146, to cause a pulse or vibrating movement of a probe, portion of sensor attached to the probe, or a structure defining the first chamber 1110; (2) control an external device, such as the pump 190 of the fluid system 50-11, to increase fluid flow into the first chamber; or (3) a combination of these processes.

An agitator, such as the agitator 1146, may be employed in static systems. When a bubble gets trapped, the agitator 1146 may basically tap, shake, or vibrate the probe, portion of a sensor attached to the probe, or a housing of the sensor assembly 1100 (like the first cover 210 or the first housing 330 of the sensor assembly 200 in FIGS. 2-4. The agitator 1146 may continue to apply a force to the probe, sensor, or housing until the SACS 1150 recognizes readings from a sensor in question have returned to within an expected range.

With regards to the pump 190, the SACS 1150 may request or direct the pump 190, or the panel 198 to direct the pump 190, to increase flow to remove the air bubble from the probe. One of ordinary skill in the art will recognize that many fluid systems for pools and/or spas include energy efficient pumps that tend to be run lower speeds. All that may be required to address an issue including an air bubble may be to increase circulation of the fluid, and not necessarily a strict increase in velocity. In some examples, varying the flowrate between higher and lower levels relative to the flowrate for which the presence of an air bubble was recognized, may be sufficient. In situations where sensor assembly 1100 is installed in a fluid system that does not include a panel such as panel 198, an integrated flow meter add-on feature may be incorporated in the subject fluid system. The sensor assembly 1100 may be connected to the pump 190 and control it to increase or decrease speed. In the examples including control of the pump 190, direction or control of the operation of the pump 190 may be accomplished via RS485 connection.

Additional issues may be addressed by the SACS 1150 for the sensor assembly 1100. Specific problems may arise when a probe is exposed to or exhibits a dry condition. The probe can drift significantly when it is dry, plus it may take a long time for a probe to recover to a satisfactory operating state after coming back into wetness. In a dry state, the probe can produce a lot of faulty data, but a user or operator will likely have no way of knowing or evening assessing what is happening. One solution may be utilizing a salinity probe to determine and indicate if fluid is or is not surrounding a probe.

A salinity probe can be used for this purpose because when a dry condition occurs the salinity probe will go from detecting salt in the fluid to having no conductivity. This is different than a situation where erroneous data is produced by a give sensor because that sensor can't recognize there is an issue. A salinity probe that does not sense a presence of fluid around it cannot take a reading. Once the salinity probe stops generating a reading because it does not have conductivity, the SACS 1150 may issue an alert. Thus, salinity probes may be used to ensure probes of the sensor assembly 1100 always remain in a wet state.

In another example, one of the first or second auxiliary sensors 1142, 1144 may include a salinity probe that is within a first housing, such as first housing 330, and wrapped around the first chamber 1110. If a housing that defines the first chamber 1110 cracks, fluid may flow straight through the breach in the housing instead of accumulating and flowing around the first and second primary sensors 1120, 1126. In such a situation, a user or technician will know there is an issue because the salinity probe will not be able to take a reading.

Figure 12A:
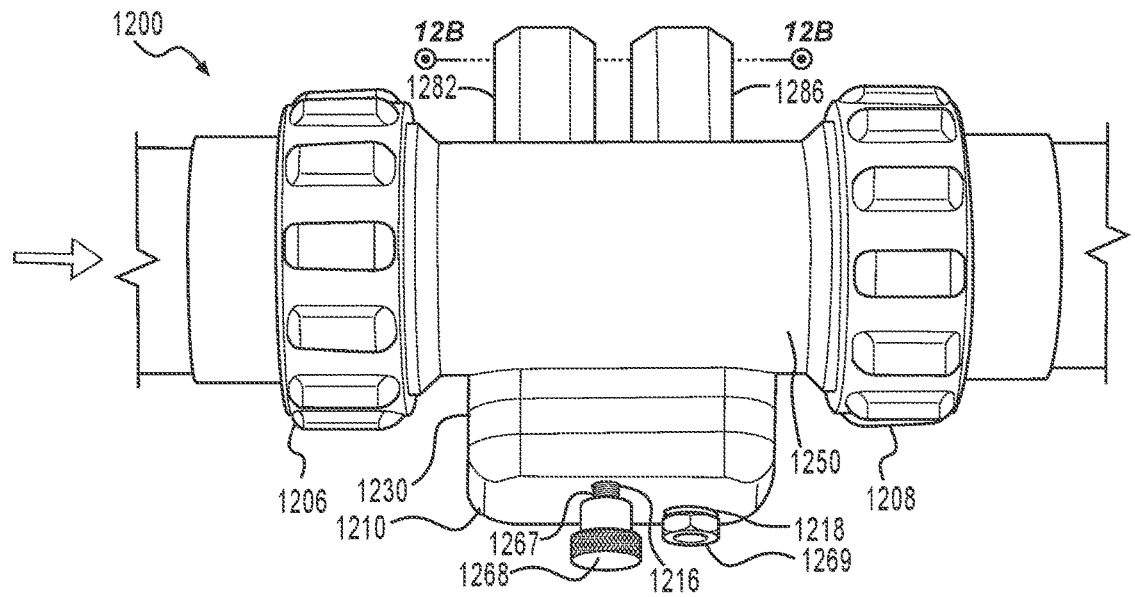
FIG. 12A illustrates a front perspective view of an exemplary sensor assembly according to an aspect of the present disclosure.
Figure 12B:
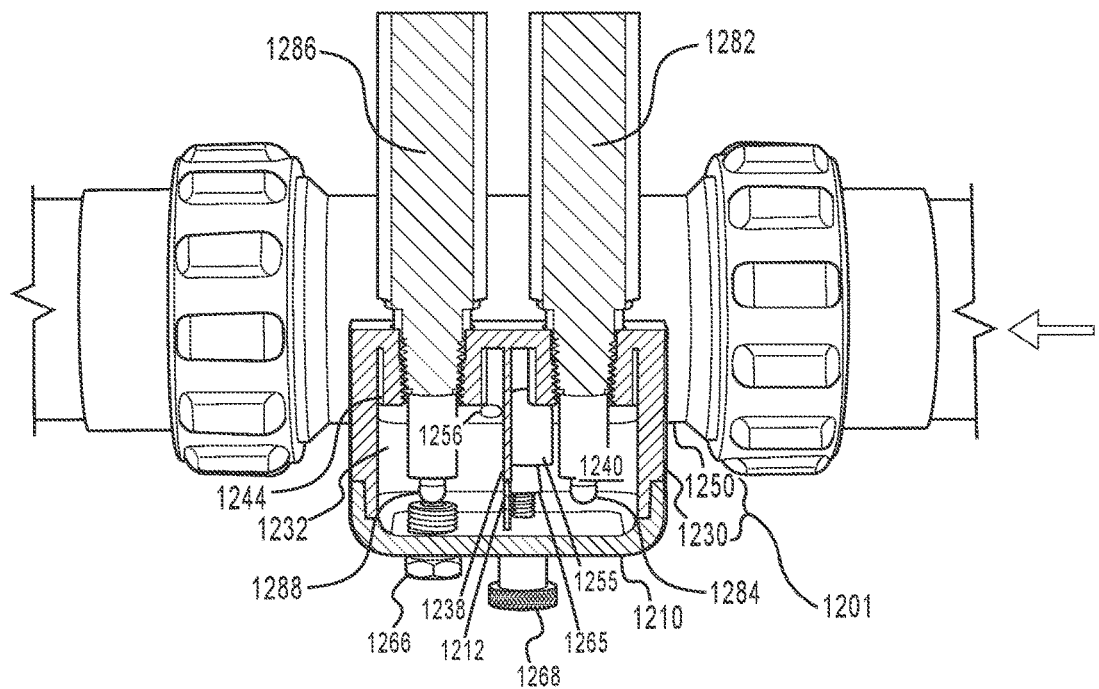
FIG. 12B is a sectional view of the sensor assembly of FIG. 12A taken from a distal plane looking out of the page as indicated by line 12B-12B.

FIG. 12A illustrates a front perspective view of an exemplary sensor assembly 1200 according to an aspect of the present disclosure. FIG. 12B is a sectional view of the sensor assembly 1200 of FIG. 12A taken from a plane indicated by line 12B-12B. As shown in FIG. 12A, the sensor assembly 1200 includes a chassis 1201 and a cover 1210. The chassis 1201 may be secured to opposing conduits by first and second adapters 1206, 1208 that attach to respective ends of the sensor assembly 1200.

As illustrated in FIG. 12B, the chassis 1201 includes first and second housings 1230, 1250. Along with the cover 1210, the first housing 1230 defines a chamber 1240 in which probes 1284, 1288 of first and second sensors 1282, 1286 may be positioned and exposed to a portion of a fluid flowing through the sensor assembly 1200. On the other hand, the second housing 1250 may define a fluid conduit through which a majority of fluid passing through the sensor assembly 1200 flows.

The first housing 1230 defines a first partition 1238 that corresponds to a second partition 1212 extending from an inner surface 1418 of the cover 1210. The first housing 1230 may further define first and second apertures 1242, 1244 disposed on opposite sides of the first partition 1238. The first and second sensors 1282, 1286 extend from an outer surface of the first housing 1230.

The cover 1210 includes a third aperture 1216 configured to receive a shaft 1268 of a valve and a fourth aperture 1218 configured to receive a plug 1269. The valve includes a knob 1268 on one end of the shaft 1267 and a valve member 1265 on an opposite end. By movement of the shaft 1267, the valve member 1265 may engage a valve port 1255. In one example, both the plug 1269 and the valve, via knob 1268, may be hand operated. In other examples, a valve actuator, such valve actuator 1090, may be attached to the sensor assembly 1200 and configured to displace the shaft 1267.

In one example, first and/or second sensor 1282, 1286 may be configured to communicate with and transmit respective readings to each other, a SACS, a panel, or another component configured to receive information from one or both of the first and second sensors 1282, 1286. In another example, the sensor assembly 1200 may include an exemplary SACS according to the present disclosure. In one example, a SACS for the sensor assembly 1200 may be incorporated into the first and/or second sensors 1282, 1286, and configured to communicate with another device such as a panel. In another example, a SACS for the sensor assembly 1200 may be a component that communicates with the first and second sensors 1282, 1286 and may be attached to or separate from the sensor assembly 1200. In other examples, the sensor assembly 1200 may include a valve actuator as discussed above, and a SACS for the sensor assembly 1200 may be incorporated in, and control, the valve actuator.

Figure 13:
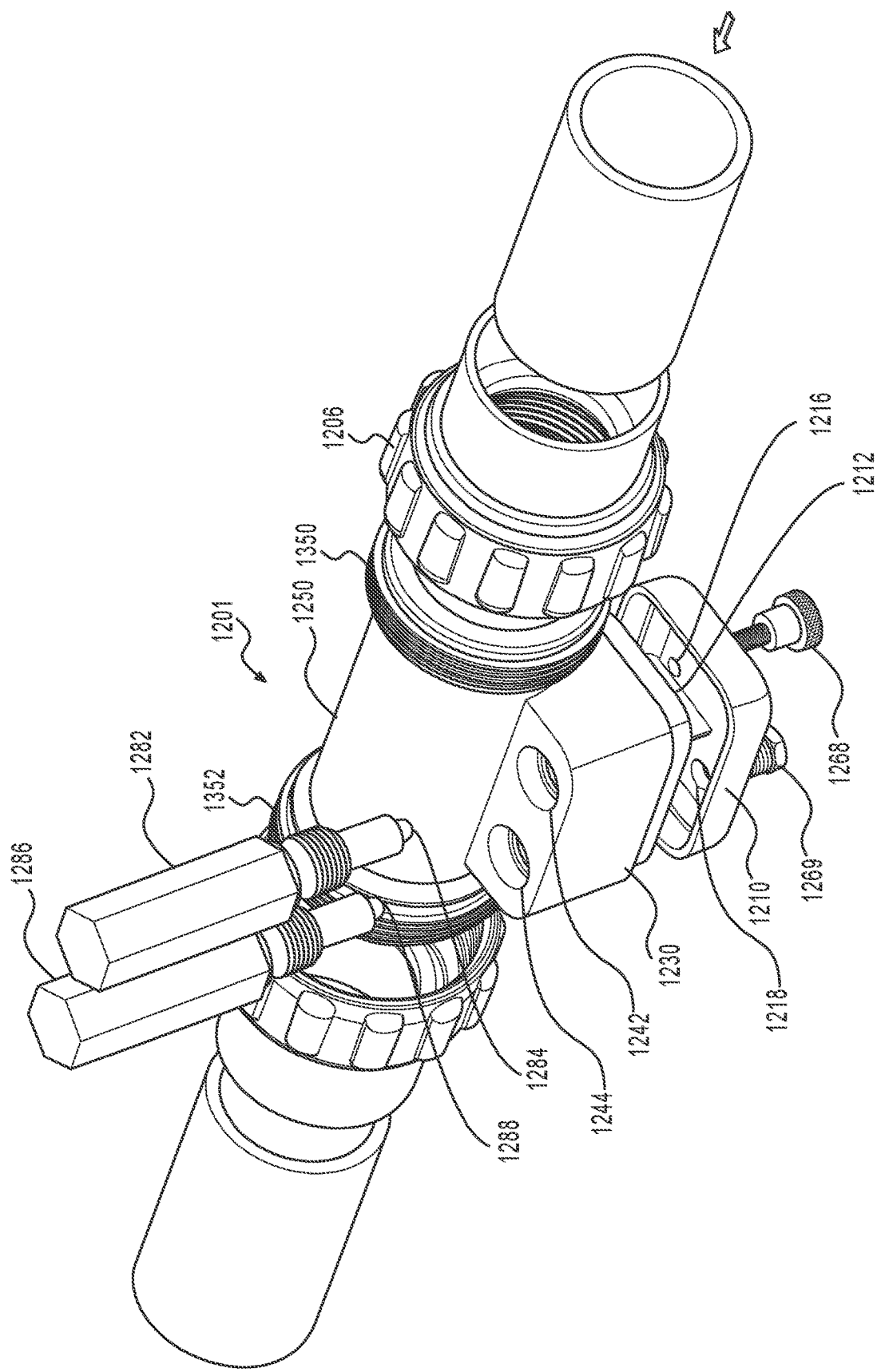
FIG. 13 illustrates an exploded view of the sensor assembly according to an aspect of the present disclosure.
Figure 14:
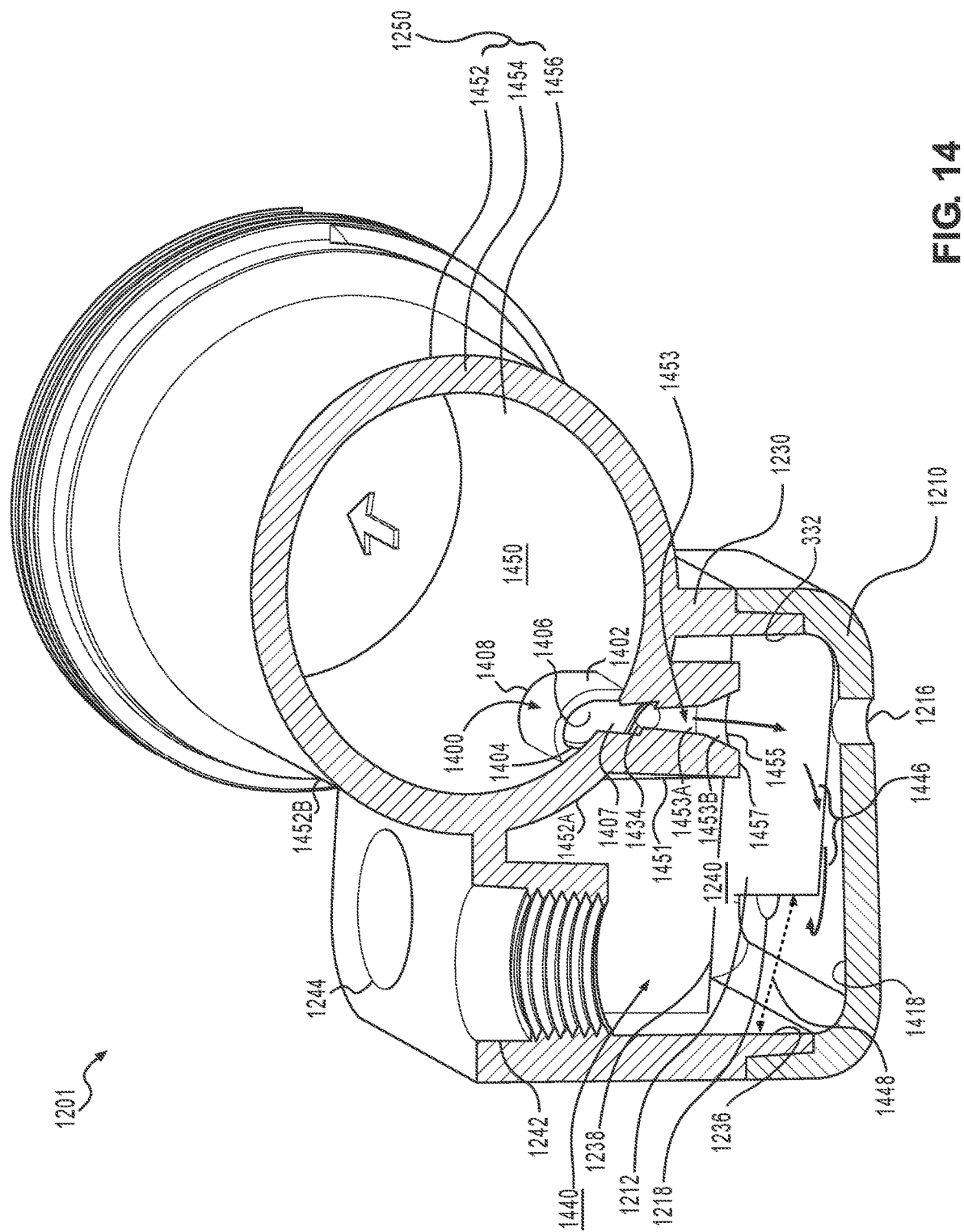
FIG. 14 illustrates a sectional view of an exemplary chassis according to an aspect of the present disclosure.

FIG. 13 illustrates an exploded view the sensor assembly 1200 of FIGS. 12A and 12B. More specifically, FIG. 13 illustrates the chassis 1201 separated from first and second sensors 1282, 1286, first and second adapters 1206, 1208, and the cover 1210 (along with the plug 1269 and the valve member 1265, shaft 1267, and knob 1268). FIG. 14, on the other hand, illustrates a sectional view of only the chassis 1201 and the cover 1210. As with FIGS. 5-7, FIGS. 13 and 14 provide views of structural aspects of the combination of the chassis 1201 and cover 1210 that provide many of the advantages common to the sensor assemblies described herein.

The chassis 1201 defines a base component to which all other components of the sensor assembly 1200 may be attached. In addition, the chassis 1201 may provide a primary mechanical feature for installing the sensor assembly 1200 in a fluid system.

The second housing 1250 of the chassis 1201, provides a component from which all other structural features or components of the sensor assembly 1200 extend from or attach to an extension of The second housing 1250 is essentially a conduit with the first and second fittings 1350, 1352 on opposite ends. Once the sensor assembly 1200 is installed, the second housing 1250 provides a section of a conduit of a fluid system. Thus, the chassis 1201 provides a mechanism for installation into a fluid system, and at the same time provides a simple configuration that enables easy and rapid replacement of individual sensors or the entire sensor assembly 1200. As discussed above with reference to FIG. 7, a user or operator may disengage the first and second adapters 1206, 1208 from the first and second fittings 1350, 1352, and take the sensor assembly 1200 out of service (possibly using a spacer such as the spacer 700) for repair or replacement.

FIG. 14 illustrates a sectional view of the chassis 1201. As shown, a body 1454 of the second housing 1250 extends from an inner surface 1456 to an outer surface 1452, is cylindrical, and defines a conduit 1450 through which fluid may flow. The outer surface 1452 of the second housing 1250 is divided by the first housing 1230 into first and second segments 1452A, 1452B. The first segment 1452A defines a wall of the chamber 1240 including the chamber outlet 1256 (see FIG. 12B). Furthermore, absent the first cover 1210, the first housing 1230 defines and open chamber 1440 as designated in FIG. 14.

The inner surface 1456 defines a diverter 1400 that protrudes into a conduit 1450 defined by the inner surface 1456 of the second housing 1250. The diverter 1400 includes a protruding wall 1402 that defines a diverter inlet 1404 along with a central wall 1406. The central wall 1406 separates the diverter inlet 1404 from the diverter outlet 1408 (see FIG. 12B). A first port 1407 is in fluid communication with the diverter inlet 1404 and extends through the body 1454 from the inner surface 1456 to a depth that may correspond to the outer surface 1452 of the second housing 1250. A chamber inlet 1434 defines an end of the first port 1407 and is in fluid communication with the valve port 1451.

The diverter outlet 1408 may also be defined within the body 1454 of the second housing 1250 and is in fluid communication with the chamber outlet 1256 via a second port (not shown) of the diverter 1400.

The diverter inlet 1404 faces against a fluid flow direction and the diverter outlet 1408 faces the same direction as a fluid flow direction. The diverter 1400 directs fluid through the chamber inlet 1434 and the valve port 1451 when the valve port is at least partially open (i.e., at least a portion the opening 1455 is not obstructed by the valve member 1265), into the chamber 1240.

As shown, a body of the valve port 1451 is part of and is otherwise defined by the chassis 1201 and includes an inner wall. The inner wall defines a bore 1453 extending from the chamber inlet 1434 to the opening 1455 in an end face 1457 of the valve port 1451. As defined by the inner wall of the valve port 1451, the bore 1453 may have different diameters as shown. More specifically, the bore may include channel 1453A and valve seat 1453B portions. The channel 1453A may extend from the chamber inlet 1434 to a transition providing an upper end of the valve seat 1453B. In one example, a diameter of the valve seat 1453B may increase along a direction from the transition to the end face 1457 where the valve seat 1453B terminates (or starts depending on one's perspective) with the opening 1455. A profile of the valve seat 1453B may correspond to a structure of the valve member 1265. In this arrangement, the valve seat 1453B may be configured to engage and stop a movement of the valve member 1265.

The first partition 1238, as a sub-structure of the chassis, extends from a first wall 1232 of the first housing 1230, across an entirety of the chamber 1240, to a second wall 1236 of the first housing 1230. The second partition 1212 extends from a wall of the first cover 1210 corresponding to the first wall 1232 of the first housing 1230, across only a portion of the chamber 1240, and thereby defines a chamber port 1448. Subject to the valve member 1265 fully engaging the valve seat 1453B of the valve port 1451, the chamber port 1448 ensures fluid communication is maintained between the chamber inlet 1434 and the chamber outlet 1256.

An inflow portion of a fluid passage 1446 is shown in FIG. 14. The fluid passage 1446 is defined by the diverter inlet 1404, the first port 1407, chamber inlet 1434, the channel 1453A, the valve seat 1453B, the opening 1455, first and second partitions 1238, 1212, the chamber port 1448, first and second walls 1232, 1234 of the first housing 1230, the inner surface 1456 of the cover 1210, the chamber outlet 1256, second port (not shown), and the diverter outlet 1408. Thus, the fluid passage 1446 is substantially defined by the chassis 1201. All the potential variations for port, inlet, or outlet sizing previously mentioned with respect other exemplary sensor assemblies described herein, may apply to the chassis 1201 illustrated in FIG. 14.

The second partition 1212 and the chassis 1201, as it defines or otherwise provides the diverter 1400, the first partition 1238, and a substantial portion of the chamber 1240, are configured to allow fluid to flow through the chamber 1240 and around the sensor probes 1284, 1288 along a simple flow path (fluid passage 1446) that does not promote turbulent fluid flow nor generation of air bubbles.

One of ordinary skill in the art will recognize that the chassis 1201 provides a central structural element of the sensor assembly 1200 and enables substantially all functionalities of the sensor assembly 1200.

In one aspect, the first and second housings 1230, 1250 of the chassis 1201 define a substantial portion of the chamber 1240 and the fluid passage 1446. The fluid passage 1446 facilitates flow of fluid from the diverter 1400, past the probes 1284, 1288, and out of the chamber 1240 through the diverter outlet 1408.

In addition, the chassis 1201 provides a compact fluid sampling system. More specifically, the diverter 1400 is built into the chassis 1201 and is directly in a flow of fluid as it flows through a fluid system. The diverter 1400 directs the fluid a short distance to sensors and through the fluid passage 1446. This substantially eliminates any opportunity for a tested portion of fluid to be contaminated or altered in any way from its composition prior to flowing through the sensor assembly 1200.

Still further, the chassis 1201 enables rapid and uncomplicated procedures for accessing and repairing or replacing critical components of the sensor assembly 1200 such as the first and second sensors 1282, 1286, as well as for maintaining the chamber 1240. The chassis defines the first and second apertures that facilitate rapid access, removal, and re-installation of primary sensors provided by the sensor assembly 1200.

Other examples of the disclosure will be apparent to those skilled in the art from consideration of the specification and practice of the examples disclosed herein. Though some of the described methods have been presented as a series of steps, it should be appreciated that one or more steps can occur simultaneously, in an overlapping fashion, or in a different order. The order of steps presented are only illustrative of the possibilities and those steps can be executed or performed in any suitable fashion. Moreover, the various features of the examples described here are not mutually exclusive. Rather any feature of any example described here can be incorporated into any other suitable example. It is intended that the specification and examples be considered as exemplary only, with a true scope and spirit of the disclosure being indicated by the following claims.

What is claimed is:

1. A chassis comprising:
   a first housing including a first wall, a second wall, and side walls that define a chamber that is open at one end;
   a second housing including an inner surface, an outer surface, and a body extending between the inner surface and the outer surface, wherein:
      the inner surface defines a conduit that extends along a longitudinal axis of the second housing,
      the body defines first and second ports that that extend through the body, and
      the outer surface is attached to the first housing;
   a central wall extending from the inner surface between the first port and the second port;
   a protruding wall extending inwardly from the inner surface into the conduit and over the central wall; and
   a partition extending between the first wall and the second wall in a location along the longitudinal axis between the first port and the second port;
   wherein the first housing is configured to receive a first sensor that measures a first parameter of a fluid.

2. The chassis of claim 1, wherein the first housing defines a first aperture and a second aperture above the chamber, wherein the first aperture is configured to receive and secure the first sensor and the second aperture is configured to receive and secure a second sensor.

3. The chassis of claim 2, wherein the partition extends from between the first aperture and the second aperture in a direction perpendicular to the longitudinal axis.

4. The chassis of claim 1, wherein the outer surface of the second housing defines a first fitting and a second fitting on opposite ends of the second housing.

5. The chassis of claim 1, wherein the protruding wall defines a first inlet in fluid communication with the first port and a second outlet in fluid communication with the second port, wherein the inner surface defines a second inlet in fluid communication with the first port and the chamber and a first outlet that is in fluid communication with the chamber and the second port.

6. The chassis of claim 1, further comprising a valve port extending from the outer surface of the second housing into the chamber, wherein the valve port includes an inner wall that defines a channel between the first port and the chamber.

7. The chassis of claim 1, wherein the first housing defines a lip that surrounds the chamber at the one end.

8. A sensor assembly comprising:
   a chassis including:
      a first housing including a first wall, a second wall, and side walls;
      a second housing extending along a longitudinal axis and including a first inner surface, an outer surface, and a body, the body defining first and second ports that extend through the body, and
      a central wall extending from the first inner surface between the first port and the second port along the longitudinal axis;
      a protruding wall extending inwardly from the inner surface over the central wall; and
      a partition extending between the first wall and the second wall in a location along the longitudinal axis between the first port and the second port;
   a cover attached to the chassis and including a second inner surface that defines a chamber with the first, second, and sides walls of the first housing;
   a first sensor for a first fluid parameter extending into the chamber; and
   a second sensor for a second fluid parameter extending into the chamber;
   wherein the protruding wall and the partition direct a portion of fluid flowing within the second housing through the first port into the chamber and out the chamber through the second port and the first and second sensors detect values for the first and second fluid parameters for the portion of fluid.

9. The sensor assembly of claim 8, further comprising a control system configured to communicate with the first sensor and second sensor and transmit information associated with the first and second fluid parameters based on communications with the first and second sensors.

10. The sensor assembly of claim 8, further comprising first and second adapters configured to secure the second housing to conduits of a fluid system.

11. The sensor assembly of claim 10, wherein the outer surface defines a first fitting configured to attach to the fluid system with the first adapter upstream of the first port, and wherein the outer surface defines a second fitting configured to attach to the fluid system with the second adapter downstream of the second port.

12. The sensor assembly of claim 8, wherein the first fluid parameter is power of Hydrogen ("pH") and the second fluid parameter is Oxidation Reduction Potential ("ORP").

13. The sensor assembly of claim 8, further comprising a third sensor for a third fluid parameter different from the first fluid parameter and the second fluid parameter, wherein the third parameter is one of a level of salinity and a temperature for the chamber.

14. The sensor assembly of claim 8, further comprising:
   a valve port extending from the outer surface of the second housing into the chamber,
   a valve member attached to a shaft that extends through the cover from the chamber to an area outside of the sensor assembly,
   wherein the valve port includes an inner wall that defines a channel and a valve seat disposed between the first port and the chamber, and
   wherein the shaft is configured to move the valve member into engagement with the valve seat and close fluid communication between the first port and the chamber.

15. A method of measuring parameters of fluid flow, the method comprising:
   installing a sensor assembly in a fluid system in an inline arrangement;
   wherein the sensor assembly includes a chassis, a cover, and first and second sensors attached to the chassis;
   wherein chassis includes:

a first housing including a first wall, a second wall, and side walls;

a second housing extending along a longitudinal axis and including a first inner surface, an outer surface, and a body, the body defining first and second ports that extend through the body, and a central wall extending from the first inner surface between the first port and the second port;

a protruding wall extending inwardly from the inner surface over the central wall; and a partition extending between the first wall and the second wall in a location along the longitudinal axis between the first port and the second port;

wherein the cover is attached to the chassis and includes a second inner surface that defines a chamber with the first, second, and side walls of the first housing;

operating the first and second sensors as a fluid flows through the sensor assembly as part of the fluid system; and transmitting information associated with the first and second fluid parameters based on operations of the first and second sensors;

wherein operating the first and second sensors includes directing a portion of the fluid to the first and second sensors as the fluid flows through the second housing, and wherein directing the portion of the fluid includes directing the portion with the protruding wall, the central wall, and the partition into the chamber, past the first and second sensors, and out of the chamber.

16. The method of claim 15, further comprising operating a third sensor of the sensor assembly and detecting one of a temperature and a level of salinity associated with the chamber.

17. The method of claim 15, wherein the transmitting includes transmitting the information associated with the first and second fluid parameters with a control system of the sensor assembly based on communications between the control system and the first and second sensors.

18. The method of claim 17, wherein the first fluid parameter is power of Hydrogen ("pH") and the second fluid parameter is Oxidation Reduction Potential ("ORP"), and wherein operating the first and second sensor includes staging, with the control system, times when pH is measured by the first sensor relative to times when ORP is measured by the second sensor.

19. The method of claim 17, further comprising:
determining, with the control system, values for one of the first and second fluid parameters are outside a respective expected range of values; and
operating, with the control system, an agitator to apply a force to one of the first sensor, the second sensor, and the first housing.

20. The method of claim 17, further comprising:
determining, with the control system, values for one of the first and second fluid parameters are outside a respective expected range of values; and
operating, with the control system, a valve actuator to restrict fluid communication between the first port and the chamber.

* * * * *